(12) United States Patent
Chou et al.

(10) Patent No.: US 7,273,743 B2
(45) Date of Patent: Sep. 25, 2007

(54) MODIFIED BACE

(75) Inventors: Kuo-Chen Chou, Kalamazoo, MI (US); W. Jeffrey Howe, Kalamazoo, MI (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 279 days.

(21) Appl. No.: 10/372,473

(22) Filed: Feb. 21, 2003

(65) Prior Publication Data

US 2004/0005691 A1 Jan. 8, 2004

Related U.S. Application Data

(60) Provisional application No. 60/358,651, filed on Feb. 21, 2002.

(51) Int. Cl.
| | |
|---|---|
| C12N 9/64 | (2006.01) |
| C12N 1/21 | (2006.01) |
| C12N 5/10 | (2006.01) |
| C12N 15/63 | (2006.01) |
| C07H 21/04 | (2006.01) |

(52) U.S. Cl. .............. 435/226; 435/252.3; 435/252.33; 435/320.1; 435/325; 435/410; 536/23.2

(58) Field of Classification Search ................ 435/226, 435/252.3, 320.1, 325; 536/23.2
See application file for complete search history.

(56) References Cited

U.S. PATENT DOCUMENTS

| 5,744,346 A | 4/1998 | Chrysler et al. ............ 435/226 |
| 6,319,689 B1 | 11/2001 | Powell et al. ............... 435/69.1 |
| 6,323,326 B1 | 11/2001 | Dorin et al. ................. 530/412 |

FOREIGN PATENT DOCUMENTS

| WO | 9822597 | 5/1998 |
| WO | 0017369 | 3/2000 |
| WO | 0047618 | 8/2000 |
| WO | 0100663 | 1/2001 |
| WO | 0123533 | 4/2001 |
| WO | 0150829 | 7/2001 |

OTHER PUBLICATIONS

Chou (2004) Journal of Proteome Research, vol. 3, No. 5, pp. 1069-1072.*
Yan, Riqiang, et al; Membrane-anchored aspartyl protease with Alzheimer's disease β secretase activity; Nature, vol. 402, pp. 533-537, Dec. 2, 1999.
Vassar, Robert, et al; β-Secretase Cleavage of Alzheimer's Amyloid Precursor Protein by the Transmembrane Aspartic Protease BACE; Science, vol. 286, pp. 733-741, Oct. 22, 1999.
Sinha, Sukanto, et al; Purification and cloning of amyloid precursor protein β-secretase from human brain; Nature, vol. 402, 537-540, Dec. 2, 1999.
Mallender, William; Characterization of Recombinant, Soluble β-Secretase from an Insect Cell Expression System; Molecular Pharmacology; 59: 619-626, 2001.
Benjannet, Suzanne, et al; Post-translational Processing of β-Secretase (β-Amyloid-converting Enzyme) and it Ectodomain Shedding; The Journal of Biological Chemistry, vol. 276, No. 14, 10879-10887, Apr. 6, 2001.
Capell, Anja, et al; Maturation of Pro-peptide Cleavage of β -Secretase; The Journal of Biological Chemistry, vol. 275, No. 40, pp. 30849-30854, Oct. 6, 2000.
Charlwood, Joanne, et al; Characterization of the Glycosylation Profiles of Alzheimer's β-Secretase Protein Asp-2 Expressed in a Variety of Cell Lines; The Journal of Bioological Chemistry, vol. 276, No. 20, p. 16739-16748, May 18, 2001.
Ermolieff, Jacques, et al; Proteolytic Activation of Recombinant Pro-memapsin 2(Pro-β-secretase) Studied with new Fluorogenic Substrates; Biochemistry, 39, 12450-12456, 2000.
Haniu, Mitsuru, et al; Chracterization of Alzheimer's β-Secretase Protein BACE; The Journal of Biological Chemistry; vol. 275, No. 28, pp. 21099-21106, Jul. 14, 2000.
Hussain, Ishrut, et al; Identification of a Novel Aspartic Protease (Asp 2) as β-Secretase; Molecular and Cellular, 419-427, Neuroscience; 14, 1999.
Khan, Amir, et al; Molecular mechanisms for the convesion of zymogens to active proteolytic enzymes; Protein Science, 7:815-836, (1998).
Lin, Xinli, et al; Rearranging the domains of pepsinogen; Protein Science; 4:159-166, (1995).
Lin, Xin-Li, et al; Synthesis, Purification, and Active Site Mutagenesis of Recombinant Procine Pepsinogen; The Journal of Biological Chemistry; vol. 264, No. 8, pp. 4482-4489, Mar. 15, 1989.
Lin, Xinli, et al; Human aspartic proteas emeapsin 2 cleaves the β-amyloid precursor protein; PNAS, vol. 97, pp. 1456-1460, Feb. 15, 2000.
Mildner, Ana, et al; Production of Chemokines CTAPIII and NAP/2 by Digestion of Recombinant Ubiquitin-CTAPIII with Yeast Ubiquitin C-Terminal Hydrolase and Human Immunodeficiency Virus Protease; Protein Expression and Purification vol. 16, 347-354, 1999.
Selkoe, D.J.; Cell Biology of the β-Amyloid Precursor Protein and the Genetics of alzheimer's Disease; Cold Spring Harbor Symposia on Quantatative Biology, vol. LXI, pp. 587-596, 1996.
Selkoe, Dennis J.; Translating cell biology into therapeutic advances in Alzheimer's disease; Nature, vol. 399, pp. A23-A31, Jun. 24, 1999.

(Continued)

Primary Examiner—Elizabeth Slobodyansky
(74) Attorney, Agent, or Firm—McDonnell Boehnen Hulbert & Berghoff LLP

(57) ABSTRACT

The present invention relates to recombinant human BACE polypeptides. More particularly, the invention relates to recombinant human BACE polypeptides that have a modified amino acid sequence at position 33 of the BACE sequence, as well as to polynucleotides, expression vectors, host cells, and methods for producing the modified recombinant human BACE polypeptides.

11 Claims, 5 Drawing Sheets

OTHER PUBLICATIONS

Thinakaran, Gopal, et al; *Metabolism of the "Swedish" Amyloid Precursor Protein Variant in Neuro2a (N2a) Cells*; the Journal of Biological Chemistry; vol. 271, No. 16, pp. 9390-9397, Apr. 19, 1996.

Inagami, T., et al; Prorenin, Biomed Res., vol. 1, pp. 456-475, 1980.

Schechter, Israel, et al; *On the Size of the Active Site in Proteases. I Papain*, Biochemical and Biophyscial Research Communications, vol. 27, No. 2, pp. 157-162, 1967.

Shi, Siao-Ping, et al; *The Pro Domain of β-Secretase does not Confer Strict Zymogen-like Properties but Does Assit Proper Folding of the Protease Domain*; vol. 276, No. 13, pp. 10366-10373, 2001.

Heinrikson, Robert L, et al; *The Biochemistry and Molecular Biology of Recombinant Human Renin and Prorenin*; Hypertension: Pathophysiology, Diagnosis and Management; Raven Press, Ltd., New York, pp. 1179-1196; 1990.

Hong, Lin, et al; *Structure of the Protease Domain of Memapsin2 (B-Secretase) Complexed with Inhibitor*, Science Magazine, vol. 290, pp. 150-153, Oct. 6, 2000.

Selkoe, Dennis, J.; *Alzheimer's Disease: Genes, Proteins and Therapy*, Physiological Review, vol. 81, No. 2, pp. 741-766, Apr. 2001.

\* cited by examiner

FIG. 1

Amino Acid Sequence of Human BACE

*MAQALPWLLLWMGAGVLPAHG* T$^1$QHGIRLPLR SGLGGAPLGL RLPRETDEEP
EEPGRRGSFV EMVDNLRGKS GQGYYVEMTV GSPPQTLNIL VDTGSSNFAV
GAAPHPFLHR YYQRQLSSTY RDLRKGVYVP YTQGKWEGEL GTDLVSIPHG
PNVTVRANIA AITESDKFFI NGSNWEGILG LAYAEIARPD DSLEPFFDSL
VKQTHVPNLF SLQLCGAGFP LNQSEVLASV GGSMIIGGID HSLYTGSLWY
TPIRREWYYE VIIVRVEING QDLKMDCKEY NYDKSIVDSG TTNLRLPKKV
FEAAVKSIKA ASSTEKFPDG FWLGEQLVCW QAGTTPWNIF PVISLYLMGE
VTNQSFRITI LPQQYLRPVE DVATSQDDCY KFAISQSSTG TVMGAVIMEG
FYVVFDRARK RIGFAVSACH VHDEFRTAAV EGPFVTLDME DCGYNIPQTD
ES$^{432}$ TLMTIAYV MAAICALFML PLCLMVCQWR CLRCLRQQHD DFADDISLLK

[SEQ ID NO: 1]

FIG. 2

```
                TQHGIRLPLR SGLGGAPLGL RLPRETDEEP    30
EEKGRRGSFV EMVDNLRGKS GQGYYVEMTV GSPPQTLNIL VDTGSSNFAV    80
GAAPHPFLHR YYQRQLSSTY RDLRKGVYVP YTQGKWEGEL GTDLVSIPHG   130
PNVTVRANIA AITESDKFFI NGSNWEGILG LAYAEIARPD DSLEPFFDSL   180
VKQTHVPNLF SLQLCGAGFP LNQSEVLASV GGSMIIGGID HSLYTGSLWY   230
TPIRREWYYE VIIVRVEING QDLKMDCKEY NYDKSIVDSG TTNLRLPKKV   280
FEAAVKSIKA ASSTEKFPDG FWLGEQLVCW QAGTTPWNIF PVISLYLMGE   330
VTNQSFRITI LPQQYLRPVE DVATSQDDCY KFAISQSSTG TVMGAVIMEG   380
FYVVFDRARK RIGFAVSACH VHDEFRTAAV EGPFVTLDME DCGYNIPQTD   430
ES       [SEQ ID NO: 2]                                  432
```

FIG. 3

```
            22                        46         54
            ↓                         ↓          ↓
pbsz  --------TQ  HGIRLPLRSG  LGGAPLGLRL  PRETDEEPEE  PGRRGSFVEM  VDN..LRGKS
1fkn  ----------  ----------  ----------  ----------  ₅₃-RRGSFVEM  VDN..LRGKS
            ↑17
1htr  ---AVVKVPL  KKFKSIRETM  KEKGLLGEFL  R.THKYDPAW  KYRFGDLS..  VTYEPMA.YM
3psg  ----LVKVPL  VRKKSLRQNL  IKDGKLKDFL  K.THKHNPAS  KY.FPEAAAL  IGDEPLENYL
            ↑16                                      ↑51         ↑60

74                   93
            ↓                    ↓
pbsz  GQGYYVEMTV  GSPPQTLNIL  VDTGSSNFAV  GAAPHPFL..  ..HRYYQRQL  SSTYRDLRKG
1fkn  GQGYYVEMTV  GSPPQTLNIL  VDTGSSNFAV  GAAPHPFL..  ..HRYYQRQL  SSTYRDLRKG
1htr  DAAYFGEISI  GTPPQNFLVL  FDTGSSNLWV  PSVYCQSQAC  TSHSRFNPSE  SSTYSTNGQT
3psg  DTEYFGTIGI  GTPAQDFTVI  FDTGSSNLWV  PSVYCSSLAC  SDHNQFNPDD  SSTFEATSQE
            ↑72                  ↑91 pbsz  VYVPYTQGKW  EGELGTDLVS  IPHGPNVTVR  ANIAAITESD  KFFINGSNWE  GILGLAYAEI
1fkn  VYVPYTQGKW  EGELGTDLVS  IPHGPNVTVR  ANIAAITESD  KFFINGSNWE  GILGLAYAEI
1htr  FSLQYGSGSL  TGFFGYDTLT  V.QSIQVPNQ  EFGLSENEPG  TNFVYAQ.FD  GIMGLAYPAL
3psg  LSITYGTGSM  TGILGYDTVQ  V.GGISDTNQ  IFGLSETEPG  SFLYYAP.FD  GILGLAYPSI 216
                                     ↓
pbsz  ARPDDSLEPF  FDSLVKQTHV  PN.LFSLHLC  GAGFPLNQSE  VLASVGGSMI  IGGIDHSLYT
1fkn  ARPDDSLEPF  FDSLVKQTHV  PN.LFSLQLC  GAGFPLNQSE  VLASVGGSMI  IGGIDHSLYT
1htr  SV..DEATTA  MQGMVQEGAL  TSPVFSVYL.  ....SNQQG.  ...SSGGAVV  FGGVDSSLYT
3psg  SA..SGATPV  FDNLWDQGLV  SQDLFSVYL.  ....SSND..  ...DSGSVVL  LGGIDSSYYT 278         289
                                   ↓           ↓
pbsz  GSLWYTPIRR  EWYYEVIIVR  VEINGQDLKM  DCKEYNYDKS  IVDSGTTNLR  LPKKVFEAAV
1fkn  GSLWYTPIRR  EWYYEVIIVR  VEINGQDLKM  DCKEYNYDKS  IVDSGTTNLR  LPKKVFEAAV
1htr  GQIYWAPVTQ  ELYWQIGIEE  FLIGGQASGW  CSEGCQ...A  IVDTGTSLLT  VPQQYMSALL
3psg  GSLNWVPVSV  EGYWQITLDS  ITMDGETIA.  CSGGCQ...A  IVDTGTSLLT  GPTSAIANIQ
                                                         ↑274

330
                        ↓
pbsz  KSIKAASSTE  KFPDGFWLGE  QLVCWQAGTT  PWNIFPVISL  YLMGEVTNQS  FRITILPQQY
1fkn  KSIKAASSTE  KFPDGFWLGE  QLVCWQAGTT  PWNIFPVISL  YLMGEVTNQS  FRITILPQQY
1htr  QATGA....Q  EDEYGQFL..  .VNCNSIQNL  PSLTF.....  ......IING  VEFPLPPSSY
3psg  SDIGA....S  ENSDGEMV..  .ISCSSIDSL  PDIVF.....  ......TIDG  VQYPLSPSAY 380                                              420
            ↓                                                ↓
pbsz  LRPVEDV...  .ATSQDDCYK  FAISQSSTGT  VMGAVIMEGF  YVVFDRARKR  IGFAVSACHV
1fkn  LRPVEDV...  .ATSQDDCYK  FAISQSSTGT  VMGAVIMEGF  YVVFDRARKR  IGFAVSACHV
1htr  I..LSN..NG  YCTVGEPTY   LSSQNGQPLW  ILGDVFLRSY  YSVYDLGNNR  VGFATAA---
3psg  I..LQD..DD  SCTSGFEGMD  VPTSSGE.LW  ILGDVFIRQY  YTVFDRANNK  VGLAPVA---

443
                       ↓
pbsz  HDEFRTAAVE  GPFVTLDMED  CGYN
1fkn  HDEFRTAAVE  GPFVTLDMED  CGYN
1htr  ----------  ----------  ----
3psg  ----------  ----------  ----
```

FIG. 4A

DNA and predicted amino acid sequence of the modified recombinant BACE expressed from pET11a-BACE-Pro33Lys construct

```
                                                          -8
Met Ala Ser Met Thr Gly Gly Gln Gln Met Gly Arg Gly Ser Met Ala Gly Val Leu Pro   -4
atg gct agc atg act ggt gga cag caa atg ggt cgc gga tcc atg gcg gga gtg ctg cct   60
                    1
Ala His Gly Thr Gln His Gly Ile Arg Leu Pro Leu Arg Ser Gly Leu Gly Gly Ala Pro   17
gcc cac ggt acc caa cat ggt att cgt ctg cca ctg cgt agc ggt ctg ggt ggt gct cca  120

Leu Gly Leu Arg Leu Pro Arg Glu Thr Asp Glu Glu Pro Glu Glu Lys Gly Arg Arg Gly   37
ctg ggt ctg cgt ctg ccc cgg gag acc gac gaa gag ccc gag gag aaa ggc cgg agg ggc  180

Ser Phe Val Glu Met Val Asp Asn Leu Arg Gly Lys Ser Gly Gln Gly Tyr Tyr Val Glu   57
agc ttt gtg gag atg gtg gac aac ctg agg ggc aag tcg ggg cag ggc tac tac gtg gag  240

Met Thr Val Gly Ser Pro Pro Gln Thr Leu Asn Ile Leu Val Asp Thr Gly Ser Ser Asn   77
atg acc gtg ggc agc ccc ccg cag acg ctc aac atc ctg gtg gat aca ggc agc agt aac  300

Phe Ala Val Gly Ala Ala Pro His Pro Phe Leu His Arg Tyr Tyr Gln Arg Gln Leu Ser   97
ttt gca gtg ggt gct gcc ccc cac ccc ttc ctg cat cgc tac tac cag agg cag ctg tcc  360

Ser Thr Tyr Arg Asp Leu Arg Lys Gly Val Tyr Val Pro Tyr Thr Gln Gly Lys Trp Glu  117
agc aca tac cgg gac ctc cgg aag ggc gtg tat gtg ccc tac acc cag ggc aag tgg gaa  420

Gly Glu Leu Gly Thr Asp Leu Val Ser Ile Pro His Gly Pro Asn Val Thr Val Arg Ala  137
ggg gag ctg ggc acc gac ctg gta agc atc ccc cat ggc ccc aac gtc act gtg cgt gcc  480

Asn Ile Ala Ala Ile Thr Glu Ser Asp Lys Phe Phe Ile Asn Gly Ser Asn Trp Glu Gly  157
aac att gct gcc atc act gaa tca gac aag ttc ttc atc aac ggc tcc aac tgg gaa ggc  540

Ile Leu Gly Leu Ala Tyr Ala Glu Ile Ala Arg Pro Asp Asp Ser Leu Glu Pro Phe Phe  177
atc ctg ggg ctg gcc tat gct gag att gcc agg cct gac gac tcc ctg gag cct ttc ttt  600

Asp Ser Leu Val Lys Gln Thr His Val Pro Asn Leu Phe Ser Leu Gln Leu Cys Gly Ala  197
gac tct ctg gta aag cag acc cac gtt ccc aac ctc ttc tcc ctg cag ctt tgt ggt gct  660

Gly Phe Pro Leu Asn Gln Ser Glu Val Leu Ala Ser Val Gly Gly Ser Met Ile Ile Gly  217
ggc ttc ccc ctc aac cag tct gaa gtg ctg gcc tct gtc gga ggg agc atg atc att gga  720

Gly Ile Asp His Ser Leu Tyr Thr Gly Ser Leu Trp Tyr Thr Pro Ile Arg Arg Glu Trp  237
ggt atc gac cac tcg ctg tac aca ggc agt ctc tgg tat aca ccc atc cgg cgg gag tgg  780

Tyr Tyr Glu Val Ile Ile Val Arg Val Glu Ile Asn Gly Gln Asp Leu Lys Met Asp Cys  257
tat tat gag gtc atc att gtg cgg gtg gag atc aat gga cag gat ctg aaa atg gac tgc  840

Lys Glu Tyr Asn Tyr Asp Lys Ser Ile Val Asp Ser Gly Thr Thr Asn Leu Arg Leu Pro  277
aag gag tac aac tat gac aag agc att gtg gac agt ggc acc acc aac ctt cgt ttg ccc  900

Lys Lys Val Phe Glu Ala Ala Val Lys Ser Ile Lys Ala Ala Ser Ser Thr Glu Lys Phe  297
aag aaa gtg ttt gaa gct gca gtc aaa tcc atc aag gca gcc tcc tcc acg gag aag ttc  960
```

FIG. 4B

| | | | | | | | | | | | | | | | | | |
|---|---|---|---|---|---|---|---|---|---|---|---|---|---|---|---|---|---|
| Pro | Asp | Gly | Phe | Trp | Leu | Gly | Glu | Gln | Leu | Val | Cys | Trp | Gln | Ala | Gly | Thr | Thr | Pro | Trp | 317 |
| cct | gat | ggt | ttc | tgg | cta | gga | gag | cag | ctg | gtg | tgc | tgg | caa | gca | ggc | acc | acc | cct | tgg | 1020 |

| Asn | Ile | Phe | Pro | Val | Ile | Ser | Leu | Tyr | Leu | Met | Gly | Glu | Val | Thr | Asn | Gln | Ser | Phe | Arg | 337 |
| aac | att | ttc | cca | gtc | atc | tca | ctc | tac | cta | atg | ggt | gag | gtt | acc | aac | cag | tcc | ttc | cgc | 1080 |

| Ile | Thr | Ile | Leu | Pro | Gln | Gln | Tyr | Leu | Arg | Pro | Val | Glu | Asp | Val | Ala | Thr | Ser | Gln | Asp | 357 |
| atc | acc | atc | ctt | ccg | cag | caa | tac | ctg | cgg | cca | gtg | gaa | gat | gtg | gcc | acg | tcc | caa | gac | 1140 |

| Asp | Cys | Tyr | Lys | Phe | Ala | Ile | Ser | Gln | Ser | Ser | Thr | Gly | Thr | Val | Met | Gly | Ala | Val | Ile | 377 |
| gac | tgt | tac | aag | ttt | gcc | atc | tca | cag | tca | tcc | acg | ggc | act | gtt | atg | gga | gct | gtt | atc | 1200 |

| Met | Glu | Gly | Phe | Tyr | Val | Val | Phe | Asp | Arg | Ala | Arg | Lys | Arg | Ile | Gly | Phe | Ala | Val | Ser | 397 |
| atg | gag | ggc | ttc | tac | gtt | gtc | ttt | gat | cgg | gcc | cga | aaa | cga | att | ggc | ttt | gct | gtc | agc | 1260 |

| Ala | Cys | His | Val | His | Asp | Glu | Phe | Arg | Thr | Ala | Ala | Val | Glu | Gly | Pro | Phe | Val | Thr | Leu | 417 |
| gct | tgc | cat | gtg | cac | gat | gag | ttc | agg | acg | gca | gcg | gtg | gaa | ggc | cct | ttt | gtc | acc | ttg | 1320 |

| Asp | Met | Glu | Asp | Cys | Gly | Tyr | Asn | Ile | Pro | Gln | Thr | Asp | Glu | Ser | End | 432 | [SEQ ID NO:7] |
| gac | atg | gaa | gac | tgt | ggc | tac | aac | att | cca | cag | aca | gat | gag | tca | | 1365 | [SEQ ID NO:8] |

MODIFIED BACE

MODIFIED BACE

This application claims priority to U.S. Provisional Patent Application Ser. No. 60/358,651, filed Feb. 21, 2002.

FIELD OF THE INVENTION

The invention is related to a recombinant human BACE. More particularly, the invention is related to an active human BACE having a modification at amino acid position 33.

BACKGROUND OF THE INVENTION

Alzheimer's disease (AD) is a progressive degenerative disease of the brain primarily associated with aging. Clinical presentation of AD is characterized by loss of memory, cognition, reasoning, judgment, and orientation. As the disease progresses, motor, sensory, and linguistic abilities are also affected until there is global impairment of multiple cognitive functions. These cognitive losses occur gradually, but typically lead to severe impairment and eventual death in the range of four to twelve years.

Alzheimer's disease is characterized by two major pathologic observations in the brain:neurofibrillary tangles and beta amyloid (or neuritic) plaques, comprised predominantly of an aggregate of a peptide fragment know as A beta. Individuals with AD exhibit characteristic beta-amyloid deposits in the brain (beta amyloid plaques) and in cerebral blood vessels (beta amyloid angiopathy) as well as neurofibrillary tangles. Neurofibrillary tangles occur not only in Alzheimer's disease but also in other dementia-inducing disorders. On autopsy, large numbers of these lesions are generally found in areas of the human brain important for memory and cognition.

Smaller numbers of these lesions in a more restricted anatomical distribution are found in the brains of most aged humans who do not have clinical AD. Amyloidogenic plaques and vascular amyloid angiopathy also characterize the brains of individuals with Trisomy 21 (Down's Syndrome), Hereditary Cerebral Hemorrhage with Amyloidosis of the Dutch-Type (HCHWA-D), and other neurogenerative disorders. Beta-amyloid is a defining feature of AD, now believed to be a causative precursor or factor in the development of the disease. Deposition of A beta in areas of the brain responsible for cognitive activities is a major factor in the development of AD. Beta-amyloid plaques are predominantly composed of amyloid beta peptide (A beta, also sometimes designated betaA4). A beta peptide is derived by proteolysis of the amyloid precursor protein (APP) and is comprised of 39–42 amino acids. Several proteases called secretases are involved in the processing of APP.

Cleavage of APP at the N-terminus of the A beta peptide by beta-secretase and at the C-terminus by one or more gamma-secretases constitutes the beta-amyloidogenic pathway, i.e. the pathway by which A beta is formed. Cleavage of APP by alpha-secretase produces alpha-sAPP, a secreted form of APP that does not result in beta-amyloid plaque formation. This alternate pathway precludes the formation of A beta peptide. A description of the proteolytic processing fragments of APP is found, for example, in U.S. Pat. Nos. 5,441,870; 5,721,130; and 5,942,400.

An aspartyl protease has been identified as the enzyme responsible for processing of APP at the beta-secretase cleavage site. The beta-secretase enzyme has been disclosed using varied nomenclature, including BACE, Asp, and Memapsin. See, for example, Sinha et.al., 1999, *Nature* 402:537–554 (p501) and published PCT application WO00/17369.

Several lines of evidence indicate that progressive cerebral deposition of beta-amyloid peptide (A beta) plays a seminal role in the pathogenesis of AD and can precede cognitive symptoms by years or decades. See, for example, Selkoe, 1991, *Neuron* 6:487. Release of A beta from neuronal cells grown in culture and the presence of A beta in cerebrospinal fluid (CSF) of both normal individuals and AD patients has been demonstrated. See, for example, Seubert et al., 1992, *Nature* 359:325–327.

It has been proposed that A beta peptide accumulates as a result of APP processing by beta-secretase, thus inhibition of this enzyme's activity is desirable for the treatment of AD. In vivo processing of APP at the beta-secretase cleavage site is thought to be a rate-limiting step in A beta production, and is thus a therapeutic target for the treatment of AD. See for example, Sabbagh, M., et al., 1997, *Alz. Dis. Rev.* 3, 1–19.

Published international patent applications WO 00/47618, WO 01/23533 and WO 00/17369 identify the beta-secretase enzyme and various methods of its use. To better understand the mechanism of action of β-secretase and help explore novel strategies for drug discovery for Alzheimer's disease, it has become important to elucidate the 3-dimensional structure of its zymogen. From the 3-dimensional structure, it has been possible to explore possible mutations in BACE which will inhibit enzyme activity as well as explore potential active site for target molecules.

SUMMARY OF THE INVENTION

The present invention relates to an isolated polypeptide sequence comprising human BACE having the modification Pro33Lys. The polypeptide can comprise at least a portion of the transmembrane domain, at least a portion of the C-terminal tail, and/or at least a portion of the signal peptide.

The invention also relates to a composition comprising an active human BACE enzyme comprising the pro-enzyme sequence of BACE having the modification Pro33Lys. The polypeptide can comprise at least a portion of the transmembrane domain, at least a portion of the c-terminal tail, and/or at least a portion of the signal peptide.

Further, the invention relates to an isolated polypeptide of SEQ ID NO: 2.

The invention relates to an isolated polynucleotide comprising a polynucleotide sequence which, by virtue of the degeneracy of the genetic code, encodes P33K-BACE. The P33K-BACE can have the sequence of SEQ ID NO: 2. The isolated polynucleotide can comprise the nucleotide sequence of nucleotides 70–1365 of SEQ ID NO: 8.

The invention also relates to an expression vector comprising the polynucleotide sequence encoding P33K-BACE. The expression vector produces a P33K-BACE polypeptide when said expression vector is present in a compatible host cell. The expression vector can comprise the polypeptide sequence of SEQ ID NO: 2.

A recombinant host cell comprising the expression vector having the polynucleotide sequence encoding P33K-BACE.

A method for producing a P33K-BACE polypeptide comprising culturing the recombinant host cell having an expression vector encoding P33K-BACE under conditions sufficient for the production of said polypeptide and recovering the polypeptide from the culture. The host cell can be *E. Coli*.

A method of producing active P33K-BACE comprising recovering the P33K-BACE from the culture of host cells according and diluting the polypeptide 20–50 fold with water having a temperature of about 1 to 15° C.

BRIEF DESCRIPTION OF THE FIGURES

FIG. 1 shows the amino acid sequence of human BACE [SEQ ID NO: 1]

FIG. 2 shows the amino acid sequence of an embodiment of the P33K-BACE polypeptide [SEQ ID NO: 2].

FIG. 3 shows a sequence alignment of β-secretase zymogen (pbsz) [SEQ ID NO: 3], β-secretase (1fkn) [SEQ ID NO: 4], progastricsin (1htr) [SEQ ID NO: 5] and pepsinogen (3 psg) [SEQ ID NO: 6]. The lines indicate the residue pair involved in forming disulfide bond as observed in 1fkn. The codes representing the conserved residues at the active site for the aspartyl protease family are residues 93–95 and residues 289–291 for pbsz, residues 91–93 and residues 274–276 for 3psg, and residues 91–93 and residues 276–278 for 1htr. The signal peptide segments (residues 1–21 for pbsz, residues 1–16 for 1 htr, and residues 1–15 for 3 psg) were not included for the alignment operation because they will be cleaved off by signal peptidase during the secretory process.

FIGS. 4A and 4B are the DNA and predicted amino acid sequence of the modified recombinant BACE expressed from a pET11a-P33K-BACE construct: amino acid sequence [SEQ ID NO: 7]; DNA sequence [SEQ ID NO: 8].

DETAILED DESCRIPTION

The invention provides for a human BACE polypeptide having a mutation at amino acid position 33 (position 54 if the leader sequence is counted). "BACE" (beta-site APP-cleaving enzyme), refers to an enzyme that mediates cleavage at the beta-site of APP. This enzyme is also known as beta-secretase, Asp2, and Memapsin 2. BACE has been described, for example, in WO 00/17369, WO 00/47618 and WO 01/23533, each of which is incorporated herein by reference in their entirety. BACE comprises an aspartyl protease and contains the classical consensus aspartyl protease active site motif (DTG/DSG).

Features of the human BACE polypeptide shown in FIG. 1 include a 21 amino acid leader (signal or pre-) sequence shown in italics, and a 24 amino acid pro-sequence, shown in bold type. $T^1$ marks the start of the pro-sequence. A 27 amino acid transmembrane domain is underlined, and is followed by the cytosolic C-terminal tail. Disulphide bridges are formed by cysteines ($Cys^{195}$–$Cys^{399}$, $Cys^{257}$–$Cys^{422}$; and $Cys^{309}$–$Cys^{359}$). For the purposes of this invention BACE may optionally include (1) the complete, or a portion of, the signal sequence at the N-terminus, (2) the complete, or a portion of, the transmembrane domain, and/or (3) the complete transmembrane domain with the complete, or a portion of, the C-terminal tail. "A portion of" refers to any number of amino acids in the various sequences.

"Pro33Lys-BACE," or "P33K-BACE", refers to the enzyme including the polypeptide sequence of recombinant human BACE having a proline to lysine mutation at position 33 as shown in FIG. 2. Accordingly, when appropriately refolded, recombinant P33K-BACE is an active BACE enzyme including a peptide sequence of at least amino acids 1–432 of BACE with the P33K mutation. Pro33Lys-BACE and P33K-BACE refer to the polypeptide as it may optionally include (1) the complete, or a portion of, the signal sequence at the N-terminus, (2) the complete, or a portion of, the transmembrane domain, and/or (3) the complete transmembrane domain with the complete, or a portion of, the C-terminal tail. "A portion of" refers to any number of amino acids in the various sequences.

The "beta secretase zymogen" or the "BACE zymogen" refers to the BACE which includes the 24 amino acid pro-sequence. Generally, an enzyme will be inactivated by the existence of its pro-peptide. However, unlike most other zymogens, the existence of the pro-peptide does not seem to have a significant impact on the activity of BACE. To understand the effect of the pro-sequence in BACE, the three dimensional structure of BACE was elucidated. From the three dimensional structure, it has been possible to explore possible mutations in BACE which will inhibit enzyme activity.

As a first step in the elucidation of the three-dimensional structure of the β-secretase zymogen, a sequence alignment was performed for the β-secretase zymogen as disclosed by Vassar et al., 1999, *Science* 286:735–741 (abbreviated as pbsz) [SEQ ID NO: 3], β-secretase (1fkn) [SEQ ID NO: 4], progastricsin (1htr) [SEQ ID NO: 5], and pepsinogen (3psg) [SEQ ID NO: 6] was performed using the PILEUP program in the GCG package (Genetic Computer Group, Madison, Wis.). Pepsinogen and progastricsin are pro-enzymes in the family of aspartyl proteases that includes β-secretase. The aligned result is given in FIG. 3, where the pro-peptides are underlined. For the case of pbsz, the signal peptide includes residues 1–21 (not shown), the pro-peptide includes residues 22–45 (Bennett, et al, 2000, *Journal of Biological Chemistry* 275:37712–37717), and the main-chain includes residues 46–446 (with the active site aspartates at 93 and 289). The transmembrane and intracellular domains that follow residue 446 are outside the scope of the study.

The numbering of amino acids in sequence pbsz of FIG. 3, and the numbering of the corresponding amino acids in FIGS. 1 and 2 differ since the numbering of FIG. 3 assumes the 21 amino acid signal sequence that is shown in italics in FIG. 1. Accordingly, position 54 of pbsz in FIG. 3 is same as position 33 in FIGS. 1 and 2. Thus, while P33K-refers to the proline to lysine mutation at position 33 of BACE as shown in FIG. 1, it should be understood that, if referring to pbsz of FIG. 3, the same mutation could be referred to as P54K.

Using the alignment shown in FIG. 3, the 3-D model of the β-secretase zymogen (pbsz) was constructed from (i) the X-ray coordinates of the protease domain of β-secretase (1fkn.pdb) recently determined by Hong et al., 2000, *Science* 290:150–153, and (ii) the X-ray coordinates of pepsinogen (3psg.pdb) determined by Hartsuck et al, 1992, *PROTEINS. Structure, Function and Genetics* 13:1–25. The pro-segment of the pepsinogen structure provided the basis for a homology model of the β-secretase pro-segment, which was grafted onto the β-secretase protease domain, using the procedure described below.

Since the pro-peptide segment and the protease domain of the model were derived from two different templates, an operation for a smooth connection at a proper site for the two structures was needed. This was performed as follows. The template structure 3psg.pdb was superimposed onto the template structure 1fkn.pdb, using the commercial software package, MOE (Chemical Computing Ltd.). During the superimposition process the entire structure of 3psg underwent a translational and rotational motion, and hence the coordinates of 3psg changed, although the coordinates of 1fkn remained unchanged. It was observed from the superimposed pair that, starting from Gly-74 and proceeding in the C-terminal direction (the residue number is counted based on the sequence of pbsz as shown in FIG. 2), the backbone chain of 1fkn followed almost the same trajectory as that of the backbone chain of 3psg, for most of the N-terminal lobe of the bilobal structures. Moving in the N-terminal direction from Gly-74 of β-secretase, however, the structures diverged markedly. Accordingly, residue 74 of the β-secretase structure became the joining point for grafting on the pro-segment of pepsinogen (in the form of the actual β-secretase pro-segment sequence). A smooth connection between residues 16–72 of 3psg and residues 74–446 of 1fkn (FIG. 2) was realized without causing any structural conflicts. The structure thus obtained was then used as a combined template to develop the final 3-D model of the β-secretase zymogen (pbsz) by the segment matching modeling method. Levitt, M., 1992, *J. Mol. Biol.* 226: 507–533.

The segment matching approach (in the MOE software) employs a database of known protein structures to build an unknown target structure based on an amino acid sequence alignment. In this case the target structure was the β-secretase zymogen, i.e. the pro-segment plus the protease domain of β-secretase. The target structure was first broken into a set of short segments. The database was then searched for matching segments on the basis of amino acid sequence similarity and compatibility with the target structure. The process was repeated 10 times and an average model was generated, followed by energy minimization of the entire pro-enzyme to create the final model. The structure thus obtained uniquely defined the atomic coordinates of not only residues 22–45, the pro-segment of pbsz, but also the segment of residues 46–55 in the main chain that was missing in the crystal structure of 1fkn.pdb (Hong et al., 2000). Furthermore, although the majority of the protease domain (residues 75–446) of pbsz was almost identical to the corresponding sequence in 1fkn, a small transition-linking part of the protease domain (residues 56–74) was affected owing to the existence of the pro-segment. This procedure was originally shown to be highly accurate for eight test proteins ranging in size from 46 to 323 residues, where the all-atom root-mean-square deviation (RMSD) of the modeled structures was between 0.93 angstrom and 1.73 angstrom (Levitt, M,. 1992, *J. Mol. Biol.* 226:507–533). This method was previously used to model the structure of the protease domain of caspase-8, at a time before the X-ray coordinates were released for caspase-3 (13). In that particular study, the atomic coordinates of the catalytic domain of caspase-3 were predicted based on the X-ray structure of caspase-1, and then the caspase-3 structure thus obtained served as a template to model the protease domain of caspase-8. After the X-ray coordinates of caspase-3 protease domain were finally released and the X-ray structure of the caspase-8 protease domain was determined (Watt, et al, 1999, *Structure* 7:1135–1143), it turned out that the RMSD for all the backbone atoms of the caspase-3 protease domain between the X-ray and predicted structures was 2.7 angstrom, while the corresponding RMSD was 3.1 angstrom for caspase-8, and only 1.2 angstrom for its core structure. This indicates that the computed structures of caspase-3 and -8 were quite close to the corresponding X-ray structures.

Since the origins of the protease domain of the model came from crystallographic coordinates, it was expected that the final energy minimized model of that domain would retain most, if not all, of the experimental attributes, and that was the case. In particular, the model retained the three pairs of disulfide bonds, i.e. $Cys^{216}$–$Cys^{420}$, $Cys^{278}$–$Cys^{443}$, and $Cys^{330}$–$Cys^{380}$. This implies that the existence of the pro-peptide segment would not destroy the disulfide bonds but rather likely facilitate a proper folding for forming the three pairs disulfide bonds as observed in an active protease domain, Haniu, M. et al, 2000, *Journal of Biological Chemistry* 275:21099–21106. Proceeding in the N-terminal direction from the pro-segment attachment point, the backbone traces a path from one end of the active site cleft, toward the center, then covers over the "flap" of the active site as described in Hong et al., 2000. It then continues toward the far end of the active site, makes a turn, and returns via two helices to near its origination point. Its overall structure is somewhat similar to the pepsinogen pro-segment from which it was derived, but with a key difference described below. An overlay of the β-secretase crystal structure with the pro-enzyme model shows some differences in side chain positioning induced by the presence of the pro-segment, and very minor differences in distal positioning, likely due to the energy minimization.

Inactivation of an enzyme by its pro-peptide is generally thought to be due to physical blockage of the catalytic site, preventing access to substrate. In the case of aspartyl proteases, a pro-segment could also disrupt the catalytically-required water molecule between the two aspartates. A comparison of the 3-D structures of pepsinogen, pro-gastricsin, and the β-secretase pro-enzyme model indicates that the pro-segments of all three cover up the catalytic site, and therefore should block access to substrate. The dynamics of protein motion, however, could allow periodic unfolding of the pro-segments exposing the catalytic clefts to enable substrate processing. Yet only for the β-secretase pro-enzyme is substrate processing known to occur, so there is something unique about the positioning of its pro-segment.

As mentioned above, the substrate amide bond hydrolysis by aspartyl proteases requires the participation of a water molecule (Silverman, R. B., 2000, The Organic Chemistry of Enzyme-Catalyzed Reactions, Chapter 2, Academic Press, San Diego). The catalytic reaction involves (i) the β-carboxyl groups of the two Asp residues (i.e., Asp-93 and Asp-289 for the case of β-secretase) at the active site being brought in to close proximity to activate a water molecule by forming hydrogen bonds with it; (ii) the nucleophilic attack of the activated water molecule on the carbonyl carbon atom of the scissile peptide bond to form the tetrahedral intermediate; (iii) the decomposition of the tetrahedral intermediate to yield the product of cleaved peptides and active enzyme. Accordingly, before a peptide bond is cleaved by an aspartyl protease, the two Asp residues at the active site must first activate a water molecule by forming four hydrogen bonds with it.

However, for the case of pepsinogen (3psg), the two active site Asp residues, i.e., Asp-91 and Asp-274 (FIG. 2), have already formed bonds to Lys-51 of the pro-peptide by two salt bridges: one is between $O^{\delta 1}$ of Asp-91 and $N^\zeta$ of Lys-51, and the other between $O^{\delta 2}$ of Asp-274 and $N^\zeta$ of Lys-51, as clearly shown in the X-ray structure determined by Hartsuck et al. As is well known, salt-bridges are stronger than hydrogen bonds. This will certainly disrupt the two active site Asp residues in activating a water molecule, and hence the activity of the pepsinogen in cleaving a peptide bond is impeded by the existence of the pro-peptide segment. A similar situation also occurs in the case of progastricsin (1htr), where the two active site Asp residues, i.e. Asp-91 and Asp-276, have also formed two salt bridges with Lys-53 of the pro-peptide: one is between $O^{\delta 1}$ of Asp-91 and $N^\zeta$ of Lys-53, and the other between $O^{\delta 2}$ of Asp-276 and $N^\zeta$ of Lys-53, as shown by the X-ray structure determined by Ivanov et al, 1990, *Biochim. Biophys. Acta*, 1040:308–310. Accordingly, one could view the salt bridges to the aspartates as a "locking" mechanism that holds the pro-segment in place and prevents the proper positioning of a catalytic water molecule.

The microenvironment is much different in the β-secretase zymogen model, where no salt bridges are observed between the pro-peptide segment and the two active site Asp residues, i.e., Asp-93 and Asp-289 (FIG. 2). According to the model, it is Pro-54 that corresponds to the Lys locations in the other two pro-enzyme structures from both sequence alignment (FIG. 2) and 3-D structure. Because the numbering of the BACE (pbsz) in FIG. 2 assumes a 21 amino acid signal sequence, Pro-54 in FIG. 2 is the same residue as Pro-33 in FIG. 1. However, a proline side-chain cannot form a salt bridge. Thus, for the case of the β-secretase zymogen, the "locking" mechanism is absent and there is no pro-segment side-chain in the location of the catalytic water position.

According to this model, therefore, the existence of the pro-peptide segment should not completely reduce the activity of β-secretase. This structural observation is supported by the recent experimental observations from the following two independent groups. Shi et al., 2001, *J. Biol. Chem.* 276:10366–10373 observed that, when assayed with a polypeptide substrate, the k(cat)/K(m) of β-secretase with the pro-segment intact is only 2.3-fold less than β-secretase. They concluded that the pro-domain of β-secretase "does not suppress activity as in a strict zymogen but does appear to facilitate proper folding of an active protease domain." Benjannet et al., (2001 *J. Biol. Chem.* 276:10879–10887), observed that "pro-BACE can produce significant quantities of Swedish mutant βAPP$_{sw}$ β-secretase product C99," and hence the pro-domain has little effect on the BACE active site.

While the absence of the "locking mechanism" in the pro-BACE model provides a possible explanation for the unusual retained activity of the pro-enzyme, the design of experiments to test the hypothesis is complicated by the fact that Pro54 (FIG. 3), or Pro33 (FIG. 1), in the pro-BACE model imparts a substantially different backbone trajectory in the region of that residue, as compared to what is observed in the two comparator crystal structures (3 psg and 1 htr). This observation would be expected, due to the cyclic conformational constraints of a proline residue. Mutation of the proline to a lysine in pro-BACE would, correspondingly, also be expected to change the backbone characteristics in that region.

As shown in the following experiments, the P33K-BACE has essentially the same activity of BACE. This suggests that confirmation of the hypothesis by experimental modification of the BACE pro-segment would need to involve more than just the Pro33Lys mutation, to include one or more additional residues that would enable the nearby pro-segment backbone to more closely mimic those of the comparator pro-enzymes.

Recombinant BACE, including recombinant P33K-BACE, can be produced, for example, in *E. coli* or other suitable host cells, by expressing a construct that contains at least a portion of a cDNA encoding P33K-BACE, for example, encoding at least a portion of the amino acid sequence shown in FIG. 2. The construct can also contain additional nucleotide sequences that may, for example, assist in purification or expression of the recombinant polypeptide, as desired.

The polynucleotide construct for expressing P33K-BACE may include nucleotides coding for the signal peptide, the transmembrane domain and/or the c-terminal tail or portions thereof. Such constructs may be assembled using routine methods by those skilled in the art. The complete polynucleotide sequence of BACE may be found, for example in Vassar et al, *Science* 286:7353–741 (1999) and the PCT publications that have been incorporated by reference herein. In addition, GenBank Accesion No. NM 012104 describes a number of known alleles of the BACE sequence. In addition, "silent" nucleotides substitutions may be introduced into the BACE construct sequence to enable better expression of the sequence in a desired organism, or for other reasons. Accordingly, due to the degeneracy of the genetic code, the polypeptide sequence of BACE may be expressed from a vast number of polynucleotide sequences. The present invention is directed to any polynucleotide sequence encoding P33K-BACE.

When expressed in *E. coli*, recombinant P33K-BACE accumulates intracellularly in an insoluble form, resulting in phase-bright inclusions in the cytoplasm (inclusion bodies). The protein in the inclusion bodies can be a mixture of monomeric and multimeric forms of the protein, both reduced and oxidized.

Processes designed to recover biologically active, soluble protein from the insoluble cellular material generally include the steps of: (1) cell lysis, (2) isolation of inclusion bodies, (3) solubilization of protein from inclusion bodies, (4) refolding of solubilized protein, and (5) purification of the active protein. Each of these steps will be described in relation to the invention below.

Useful constructs for the production of P33K-BACE are designed to express a selected portion of the P33K-BACE polypeptide. The polynucleotide encoding the P33K-BACE polypeptide can be operably linked to suitable transcriptional or translational regulatory sequences in an expression construct. Regulatory sequences include transcriptional promoters, operators, enhancers, mRNA ribosomal binding sites, and other sequences that control transcription or translation. Nucleotide sequences are "operably linked" when the regulatory sequence functionally relates to the polynucleotide encoding P33K-BACE. Thus, a promoter nucleotide sequence is operably linked to a polynucleotide encoding P33K-BACE if the promoter nucleotide sequence directs the transcription of the P33K-BACE sequence.

The polynucleotide is cloned into appropriate expression vectors for expression in *E. coli*. Generally, an expression vector will include a selectable marker and an origin of replication, for propagation in *E. coli*. Expression vectors generally comprise one or more phenotypic selectable marker genes. Such genes generally encode, for example, a protein that confers antibiotic resistance or that supplies an auxotrophic requirement.

A polynucleotide can encode a P33K-BACE polypeptide having an N-terminal methionine to facilitate expression of the recombinant polypeptide in a prokaryotic host, for example, for expression in *E. coli*. The N-terminal methionine can optionally be cleaved from the expressed P33K-BACE polypeptide. The polynucleotide can also encode other N-terminal amino acids added to the P33K-BACE polypeptide that facilitate expression in *E. coli*. Such amino acids include, but are not limited to, a T7 leader sequence, a T7-caspase 8 leader sequence, and known tags for purification such as the T7-Tag MASMTGGQQMGR [SEQ ID NO: 9] that allows binding of antibodies, or a six-histidine tag (His)$_6$ that allows purification by binding to nickel. Other useful peptide tags include the thioredoxin tag, hemaglutinin tag, and GST tag. These and other amino acid tags can be encoded by polynucleotides added to either terminus of the polynucleotide encoding P33K-BACE.

The polynucleotide of the expression construct can encode a P33K-BACE polypeptide that is truncated by removal of all or a portion of the C-terminal cytoplasmic tail, the transmembrane domain, the membrane proximal region, or any combination of these. The expression constructs can also encode cleavage sites for selected enzymes, to improve purification of the expressed protein or to assist in expression of the enzyme, when desired.

It has been found that active recombinant BACE protein can terminate at $S^{432}$, lacking the transmembrane domain and cytosolic tail region. This provides BACE in a soluble form, that is, a form that is not membrane-bound. Accordingly, in the following examples, P33K-BACE was terminated at $S^{432}$ to compare activity with the known active recombinant BACE.

For efficient expression, one or more codon of the polynucleotide sequence encoding P33K-BACE can be modified, using such techniques as site directed mutagenesis, to eliminate GC-rich regions of strong secondary structure known to interfere with efficient cloning or expression of the recombinant protein. Codons can also be optimized for expression in *E. coli*, for example, according to published codon preferences. Underlined nucleotides in FIG. 4A show preferred codon changes.

An expression construct containing a polynucleotide encoding P33K-BACE can be used to transform bacteria, for example *E. coli*, in order to produce P33K-BACE protein. Production of the protein can be inducible or constitutive, depending upon the control elements provided in the vectors. For example, expression constructs are transfected into a bacterial host, such as *E. coli* BL21 codon plus (DE3) RP (Stratagene) and grown in suitable media, such as Luria broth supplemented with 100 micrograms/ml ampicillin and 34 micrograms/ml chloromphenicol. When cells have grown to a desired density, in general, when the absorbance of the culture at 550 nm is between 0.5 and 0.6, expression is induced. For example, the T7 or T5 lac promoter promotes expression of the operably linked P33JK-BACE polynucleotide upon addition of IPTG (for example, to a final concentration of about 1 mM) to the culture media. After induction, for example, about three hours, the cell pellet is collected and can be stored, generally at −70° C., for later enzyme purification.

The expressed recombinant enzyme accumulates intracellularly in an insoluble form, as inclusion bodies. To recover the enzyme from insoluble cellular material, bacterial cells are pelleted from the bacterial cell culture, lysed, and the inclusion bodies are isolated from the lysed cells. The recombinant enzyme can then be isolated from the isolated inclusion bodies.

Generally, lysing of cells to obtain the protein inclusion bodies can be accomplished using a number of known methods, including mechanical and chemical techniques. Sonication and freeze-thaw techniques are generally not practical for the volume of cells being disrupted. However, any commercially available device that uses a pressure differential to disrupt the cells, such as a French Press or a Rannie apparatus, is acceptable, assuming the overall handling capacity is similar or greater than these instruments. Detergent solubilization is not generally a practical solution, since removal of the detergent can pose a difficult challenge and may influence subsequent refolding efforts. Detergents may solubilize contaminating proteins and nucleic acids together with some or all of the protein of interest from the inclusion bodies, and thus is not a desirable option. Once the cells have been lysed, the inclusion bodies may be washed to remove protein contaminants associated with or entrapped in the inclusion bodies. If not removed, such contaminants could interfere with or prevent refolding of the enzyme.

For example, to obtain inclusion bodies, bacterial cells can be suspended in a suitable buffer that may contain a salt such as sodium chloride, a chelating agent such as EDTA, or both. Suspended cells are then lysed using, for example, a French Press or a Rannie apparatus. The insoluble cellular material obtained is washed in buffer and can be stored and frozen at −20° C. overnight.

Protein aggregates (inclusion bodies) are solubilized and then refolded to obtain active protein. Reagents that can be used to solubilize P33K-BACE include urea, guanidine HCl, guanidine thiocyanate, and the like, generally at a concentration of about 6 to 8M. Reducing agents, such as beta-mercaptoethanol (BME), glutathione (gamma-Glu-Cys-Gly; or GSH, Sigma Cat. No. G-6529); or DTT (dithiothreitol, Sigma Cat.No. D-0632), and the like can also be used. These reducing agents can be used separately or in combination to provide the isolated protein in a reduced form (random coil). These agents can reduce the presence of dimers and higher molecular weight multimers, as well as reduce improper folding, for example, as a result of cysteine residues within the protein, or reduce aggregation of the protein.

Solubilization of P33K-BACE present in inclusion bodies can be achieved via treatment with a solubilizing agent at a high pH (about pH 10–11), and in the presence of a reducing agent such as BME. For example, the insoluble cellular material can be solubilized in 8 M urea, 1 mM EDTA, 1 mM glycine, 100 mM Tris base (pH 10.1–10.6), and 100 mM BME. An aliquot of sample is then diluted, for example, 10-fold, centrifuged, and the optical density (OD) at 280 nm is measured. Sample is diluted to adjust the OD to about 5.0 and pH to approximately 10.1. The sample is then diluted in 8 M urea buffer without a reducing agent. Thereafter, the reducing agent, for example, BME, is added to make the total molarity of the reducing agent about 10 mM. Dithiothreitol (DTT), reduced glutathione (GSH) and oxidized glutathione (GSSH) are added to the solution to obtain final concentrations of 10 mM DTT, 1 mM GSH, and 0.1 mM GSSG, and the pH of the solution is adjusted to 10.3–10.5. This procedure provides P33BACE in reduced form.

Alternatively, insoluble cellular material can be solubilized and the enzyme provided in reduced form by washing in 10 mM Tris buffer (pH 8), 1 mM EDTA (TE). Inclusion bodies are then extracted with 8 M urea, 100 mM AMPSO (pH 10.5–10.8), 1 mM glycine, 1 mM EDTA, and 100 mM BME. AMPSO is 3-[(1,1-dimethyl-2-hydroxyethyl)amino]-2-hydroxypropanesulfonic acid (Sigma Cat. No. A1911). After centrifugation, the protein concentration of the supernatant can be adjusted by dilution with buffer to approximately 5.0 at $A_{280}$. The protein is then diluted with 8 M urea, 100 mM AMPSO, 1 mM glycine, 1 mM EDTA, and BME at an adjusted concentration of 10 mM. Other buffer solutions can be substituted for AMPSO, such as CAPS or Tris. CAPS is (3-[cyclohexylamino]-1-propanesulfonic acid, Sigma Cat. No. C-2632).

Once the protein has been solubilized, it can be refolded into the correct conformation to provide active enzyme. Typically, refolding of an expressed recombinant enzyme can be accomplished by removing the solubilizing agent and replacing it with an aqueous buffer, for example, by dialysis or dilution. Generally, for proteins with disulfide bridges, oxidation of the reduced protein occurs prior to or concomitant with refolding.

According to the invention, reduced protein P33K-BACE is refolded by considerably diluting (20 to 50 fold, generally 20 to 30 fold) the enzyme in a cold, aqueous solution such as water, optionally to a final concentration of about 10 μg to 30 μg P33K-BACE per ml of solution. Water is preferred, generally at a temperature of about 4° C. to 15° C.

Generally, refolding of recombinantly expressed P33K-BACE is accomplished by permitting the diluted enzyme solution (at about pH 10–11) to rest at about 4° C.-15° C. in, for example, a coldroom or refrigerator for approximately 3–5 days.

For example, as shown in the Examples below, solubilized, recombinant P33K-BACE can be diluted in water (20–25 fold), optionally to a final concentration of approximately 10 micrograms to 30 micrograms P33K-BACE per ml of water, and generally at a pH of about 10.5–10.8. This mixture is maintained at temperatures of approximately 4° C. to approximately 15° C. for several days (3–5) and assayed periodically for enzymatic activity. Activity assays can be performed at this resting stage, starting at about 20 to 24 hours after the initial dilution step.

The refolded enzyme can be purified using standard liquid chromatography techniques, such as, for example, cation or anion exchange chromatography (available, for example, from Amersham Pharmacia Biotech), hydrophobic interaction (available, for example, from Toso Haas), dye interaction (available, for example from Sigma), ceramic hydroxyapatite (available, for example, for Bio-Rad), affinity chromatography (for example, using an inhibitor that binds active enzyme), or size exclusion chromatography (for example, Sephacryl-S100 or S200 column purification as well as resins from BioRad, Toso Haas, Sigma, and Amersham Pharmacia Biotech). One or a combination of these purification techniques can be used according to the invention to provide purified, recombinant P33K-BACE. Anion exchange chromatography using, for example, Q-sepharose, Mono-Q, or Resource Q column purification provides useful separation.

Activity of the refolded, purified recombinant P33K-BACE can be determined by incubating the refolded enzyme with a suitable substrate under conditions to allow cleavage of the substrate. The substrate can be labeled with a detectable marker, such as a fluorescent label, to allow detection of cleavage events.

Suitable substrates are peptides that include a P33K-BACE cleavage site. For example, the synthetic peptides (SEISY-EVEFRWKK) (SEQ ID NO: 10) and (GLTNIK-TEEISEISY-EVEFRWKK) (SEQ ID NO: 11) can be cleaved by the recombinant P33K-BACE (at the site marked by "–"). Additional substrates suitable for BACE cleavage include the non-limiting examples, (SEVNL-DAEFRWKK) (SEQ ID NO: 12) and (GLTNIKTEEISEVNL-DAEFR-WKK)(SEQ ID NO: 13), containing the APP Swedish Mutation.

The substrate can be labeled with a suitable detectable marker to permit visualization of cleavage. Assays to detect activity of recombinantly produced P33K-BACE can measure retention or liberation of the detectable marker. Suitable detectable markers include, for example, radioactive, enzymatic, chemiluminescent, or fluorescent labels. In some embodiments, the substrate can include internally quenched labels that result in increased detection after cleavage of the substrate. The substrate can be modified to include a paired fluorophore and quencher including, but not limited to, 7-amino-4-methyl coumarin and dinitrophenol, respectively, such that cleavage of the substrate by P33K-BACE results in increased fluorescence as a result of physical separation of the fluorophore and quencher. Other paired fluorophores and quenchers include bodipy-tetramethylrhodamine and QSY-5 (Molecular Probes, Inc.).

In a variant of this embodiment, biotin or another suitable tag can be placed on one end of the peptide to anchor the peptide to a substrate assay plate, and a fluorophore can be placed at the other end of the peptide. Useful fluorophores include those listed herein, as well as Europium labels such as W8044 (EG&G Wallac, Inc.). One exemplary label is Oregon green that can be coupled to a cysteine residue. Cleavage of the substrate by P33K-BACE will release the fluorophore or other tag from the plate, allowing detection of an increase in retained fluorescence.

Further examples of detectable markers include a reporter protein amino acid sequence coupled to the substrate. Exemplary reporter proteins include a fluorescing protein (for example, green fluorescing proteins, luciferase, and the like) or an enzyme that is used to cleave a substrate to produce a calorimetric cleavage product. Also contemplated are tag sequences that are commonly used as epitopes for quantitative assays. Preferably, the detectable markers do not interfere with binding of P33K-BACE to the substrate, or subsequent cleavage of the substrate. For example, detectable markers can be provided in a suitable size that does not interfere with P33K-BACE activity. In some embodiments, detectable markers can be coupled to the substrate using spacers.

EXAMPLES

Example 1

Cloning of P33K-BACE

An expression construct for producing recombinant P33K-BACE protein in *E. coli* was prepared by site-directed mutagenesis from an existing construct referred as pET11a-BACE. This construct contains nucleotides coding for the following sequence: T7 tag (MASMTGGQQMGR)-GSM-BACE ($A^{-8}$-$S^{432}$), where the expressed BACE fragment is truncated at both N-terminal and C-terminal regions as compared with the sequence shown on FIG. 1. The insert encodes a protein lacking the transmembrane domain and the 13 N-terminal residues of the leader sequence. A methione codon was inserted adjacent to the first BACE codon, to facilitate removal of the BACE insert with BamHI and potential subcloning for expression of the BACE sequence without the T7 tag. However, this methionine residue is not necessary if the T7 tag is included. The BACE cDNA sequence contains preferred codons for expression in *E. coli*. These codon changes are underlined in FIG. 4A.

pET11a-BACE can be prepared by techniques well known to one skilled in the art. The insert is obtained by PCR from a full length BACE cDNA. The PCR primers are designed to amplify the BACE sequence from $Ala^{-8}$ to $Ser^{432}$, including BamHI sites for insertion into the pET11a vector (Novagen, Madison, Wis.). Examples of PCR primers that can be used are:

```
PF1 5'-GGCA GGA TCC ATG GCG GGA GTG CTG CCT GCC CA    (Forward) [SEQ ID NO: 14]

PF2 5'-GGC AGG ATC CTA TGA CTC ATC TGT CTG TGG AAT G  (Reverse) [SEQ ID NO: 15]
```

The PCR product is gel-purified, digested with restriction enzymes, and ligated to the corresponding sites of vector pET11a. The vector includes the T7 lac promoter, permitting induced expression on addition of IPTG.

The codon changes (underlined on FIG. 4A) can be introduced by site directed mutagenesis, using oligonucleotide primers and PCR and the method described below for mutagenesis of P33K. These changes are not necessary for successful expression of BACE in E. coli, but may improve yield of the re-foldable protein by eliminating rare codons.

In this embodiment of the invention, the pET11a-BACE construct was derived from two pre-existing clones. One clone, referred to as pET11a-BACE-J, contained the desired codon changes but lacked the two C-terminal cysteines. The other clone referred as pQE80L-BACE (MRGS (H)$_6$ GS GSIGTD-BACE: T$^1$-S$^{432}$) contains all the required cysteins (6), but lacks Ala$^{-8}$ to Gly$^{-1}$ (pQE80L, Qiagen). Two overlapping cDNA fragments were generated by PCR. BACE-encoding polynucleotides 37 to 880 as shown in FIGS. 4A and 4B were amplified from pET11a-BACE-J, overlapping 20 nucleotides with the remaining BACE sequence, which was amplified from pQE80L-BACE (nucleotides 861–1368 which includes a stop codon not present at this position in BACE).

The PCR primers for BACE-encoding polynucleotides 37 to 880 amplification of pET11a-BACE-J were:

```
                                            [SEQ ID NO: 16]
PF3 5'-GGCA GGA TCC ATG GCT GGT GTT CTG CCA GCT

[SEQ ID NO: 17]
PR4 5'-T GCC ACT GTC CAC AAT GCT C
```

Primer PF3 includes preferred codon changes in addition to those shown in FIG. 4A.

The overlapping segment from pQE80L-BACE including the rest of the c-terminal amino acids was amplified in a separate PCR reaction, using the primers:

```
PR5-5' GGCAGGATCCTA TGA CTC ATC TGT CTG TGG AAT 3'  (reverse) [SEQ ID NO: 18]

PF6-5' G AGC ATT GTG GAC AGT GGC A 3'.              (forward) [SEQ ID NO: 19]
```

The PCR conditions were as follows: one initial cycle of denaturation at 95° C., 30 seconds, 30 cycles of 30 seconds denaturation at 95° C., 30 seconds annealing at 60° C., 2 minutes extension at 72° C., followed by one cycle of 5 minutes at 72° C. The reaction component were: 1× cloned Pfu polymerase buffer (Stratagene), 100 µM each dNTP, 100 ng each primer, 10 ng template DNA, and 2T1 (20 units) of cloned Pfu DNA polymerase.

The products obtained from these two PCR amplifications were joined together in a third PCR amplification using the external primers PF3 [SEQ ID NO: 16] and PR5 [SEQ ID NO:18]. This final product was gel purified, digested with BamIII and ligated into the corresponding site of vector pET11a.

The construct for expressing P33K-BACE was obtained by introducing the P33K mutation in pET11a-BACE by PCR using primers PF8 and PF9 as follows:

```
                              [SEQ ID NO: 20]
PF7-5' CCGAGGAGAAAGGCCGGAGGG      (forward)

[SEQ ID NO: 21]
PR8-5' CCCTCCGGCCTTTCTCCTCGG     (reverse)
```

The codons for the substitution of Lysine for Proline at amino acid position 33 are underlined. Lysine is also coded by AAG. Accordingly the forward and reverse codons could also be AAG and CTT, respectively.

The products obtained from these two PCR amplifications were joined together in a third PCR amplification using the external primers for the pET11a vector:

```
PF9-5' TAATACGACTCACTATAGG    (forward, T7 promoter)         [SEQ ID NO. 22]

PF10-5' GCTAGTTATTGCTCAGCGG   (reverse, T7 terminator primer) [SEQ ID NO. 23]
```

This final product was gel purified, digested with BamHI and ligated into the corresponding site of vector pET11a. The complete DNA and amino acid sequence for the pET11a-P33K-BACE construct is shown in FIGS. 4A and 4B. The first fifteen amino acids (underlined) correspond to the vector's T7 tag and contain a BamHI cloning site as well as an additional methionine. Codon changes as preferred for expression in E. coli are shown in bold type.

Example 2

Cell Incubation and Inclusion Body Harvest

Ligated DNA was transformed into E. coli DH5α for propagation and DNA isolation. The resulting DNA was fully sequenced in both strands and then transformed into E. coli BL21 CodonPlus (DE3) Rp for expression. Cells were grown in Luria Broth (LB), pH 7.5, with 100 µg/ml ampicillin and 34 µg/ml chloramphenicol, at 37° C. and 200 rpm (2.5 inch throw). A loop of a glycerol stock of the construct was inoculated into the media and was incubated until the $A_{550}$=0.5–0.6. Cells were collected by centrifugation, resuspended in fresh media, and used as inoculum for a secondary culture at a 1:100 dilution. When cell density reached $A_{550}$=0.5–0.6, cells were harvested by centrifugation at room temperature and then resuspended at the same concentration in fresh LB, again containing ampicillin and chloramphenicol.

P33K-BACE expression was induced by the addition of IPTG to a final concentration of 1 mM. Expression of the recombinant protein was continued for 3 hours after induction ($A_{550}$=1.8–2.0). Cells were collected by centrifugation and stored at −80° C.

To determine the level of expression and localization of the recombinant protein, the collected centrifuged cells (cell paste) was resuspended in TE (10 mM Tris HCl pH 8.0, 1 mM EDTA) at 1/10 of the original culture volume and sonicated. The soluble protein fraction was separated from cell debris and insoluble proteins by centrifugation at 10,000 ×g for 15 minutes. Protein in each of the fractions was analyzed by SDS-PAGE.

To obtain inclusion bodies, cultured cells were centrifuged to pellet the cells. Cell pellets were weighed from 1.0 liters of cell culture. The wet weight of the cell pellet was 2.25 g. The cell pellet was resuspended in 20 ml TE. The re-suspended cell pellet was subjected to 16,000 psi in a French press. The resulting solution was centrifuged at 6000 rpm for 30 minutes and then at 2900 rpm for 30 minutes in a Sorvall SS34 rotor. The pellet was then frozen at −20° C. for storage and later resuspended in 4 ml 8 M urea, 100 mM AMPSO, 1 mM glycine, 1 mM EDTA, and 100 mM BME, at pH 10.5–10.8. After centrifugation at 12,900 rpm in a Sorvall SS34 rotor for 40 minutes, the protein concentration of the supernatant was diluted 50 times with the above buffer (without BME) to read approximately 5.0–7.0 at $A_{280}$.

The P33K-BACE was refolded by diluting the resuspended protein 20–25 times with approximately 1700 ml of cold $H_2O$ and adjusting the pH to 10.1 with a few drops of HCl. This dilution was stored for approximately 3 weeks at 4–15° C. prior to purification Example 3

Purification of Refolded P33K-BACE Enzyme

A first purification step involved a Q-Sepharose™ FAST FLOW columns to concentrate the enzyme sample and remove nucleic acids present in abundance at this stage. The 1700 ml enzyme sample was loaded onto a 10 ml Q-Sepharose™ Fast Flow column was pre-equilibrated with 10 mM Tris (pH 8.2), 0.4 M urea and NaCl to bring the conductivity to 0.9 mMhos (to match the ionic strength of the BACE protein solution). A linear gradient of 0–1.0 M NaCl was applied in the same buffer used to equilibrate the column. Fractions of 5.5 ml were collected. Elutions of protein fractions were stored in a cold room.

A second purification step involved affinity purification. An affinity column was generated by coupling 1 mg of reduced Inhibitor I-1 (shown below) per ml of SulfoLink™ Coupling Gel (Pierce, Cat. No. 204011) in an Econo column (BioRad) in an amount of 1 mg/ml of the gel, according to the manufacturer's instructions.

The 36 ml BACE solution obtained from Q-Sepharose™ FAST FLOW purification was added to 9 ml of 1 M sodium acetate buffer, pH 4.5. No visible precipitate was observed. The sample was then loaded onto the affinity column pre-equilibrated with 200 mM sodium acetate buffer, pH 4.5. Elution from the affinity column was performed at pH 8.5 with 100 mM sodium borate. The eluted sample, 30 ml, was assayed for activity and analyzed on SDS-PAGE.

Example 4

Expression of BACE in CHO Cells (Control)

In order to provide a control for activity assays for P33K-BACE expressed in *E. Coli* and prepared as in Examples 1–3, a BACE construct (Asp2-2L-TM-His$_6$) encoding the amino acid sequence shown below in Table 2, was expressed in CHO cells and purified from about 75 liters of conditioned media. The purification process consisted of successive steps of tangential flow concentration, ammonium sulfate precipitation, Nickel affinity column, and affinity chromatography (I-1 affinity). However, the purified enzyme contains a 50:50 mixture of the isoforms starting at $T^1QHGIRL\ldots$, and $E^{25}TDEEPEEPG\ldots$, numbered as in FIG. 1. The two isoforms are generated by post-translational cleavage by yet unknown proteases. It is readily expected that P33K-BACE can be expressed in CHO cells following site directed mutagenisis of the BACE polynucleotide.

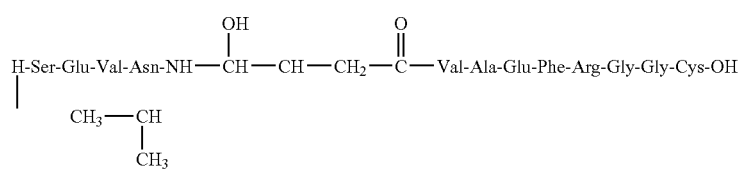

(I-1)

TABLE 1

BACE Construct Asp2-2L-TM-His$_6$

| | | | | |
|---|---|---|---|---|
| MAQALPWLLL | WMGAGVLPAH | GTQHGIRLPLR | SGLGGAPLG | LRLPRETDEE [SEQ ID NO: 24] |
| PEEPGRRGSF | VEMVDNLRGK | SGQGYYVEMTV | GSPPQTLNILV | DTGSSNFA |
| VGAAPHPFLH | RYYQRQLSST | YRDLRKGVYVP | YTQGKWEGELG | TDLVSIPH |
| GPNVTVRANI | AAITESDKFF | INGSNWEGILG | LAYAEIARPDD | SLEPFFDS |
| LVKQTHVPNL | FSLQLCGAGF | PLNQSEVLASV | GGSMIIGGIDH | SLYTGSLW |
| YTPIRREWYY | EVIIVRVEIN | GQDLKMDCKEY | NYDKSIVDSGT | TNLRLPKK |
| VFEAAVKSIK | AASSTEKFPD | GFWLGEQLVCW | QAGTTPWNIFP | VISLYLMG |
| EVTNQSFRIT | ILPQQYLRPV | EDVATSQDDCY | KFAISQSSTGT | VMGAVIME |
| GFYVVFDRAR | KRIGFAVSAC | HVHDEFRTAAV | EGPFVTLDMED | CGYNIPQT |
| DESHHHHHH | | | | |

Example 5

Activity Assay

The activity of P33K-BACE expressed in *E. coli* according the above Examples was compared to the activity of human BACE prepared as above without the P33K mutation, and to human BACE expressed in CHO cells. The results are provided in Table 2.

To assay for BACE activity, the following activity assay conditions were utilized, unless specifically indicated otherwise: 20 µl 1 M sodium acetate (NaOAc), pH 5.0; 125 µl $H_2O$; 50 µl BACE sample containing 5–10 pmoles protein; and 5 µl 1 mM substrate S-1 (SEQ ID NO: 10).

The 200 µl assay reaction was incubated for 1–2 hours at 37° C. Activity was expressed as fluorescence peak area generated by the liberation of a fluorescent (Tryptophan fluorescence) product upon cleavage of Substrate S-1 by recombinant BACE. The reaction was stopped with 100 µl of 4% TFA in $H_2O$. In order to separate the cleavage products and thereby detect activity of recombinant BACE, 50 microliters of the reaction mixture was injected into a Hewlett Packard Model 1100 HPLC equipped with an Alltech Rocket™ column (7 mm i.d.,×53 mm length, $C_{18}$, 3 µm) pre-equilibrated with 88% Reagent A (0.1% TFA in water), 12% Reagent B (0.1% TFA in acetonitrile). The flow rate over this column was 3 ml per minute.

TABLE 2

| Activity Assays (Fluorescence Peak Area) | | |
|---|---|---|
| *E. Coli* P33K-BACE | *E. Coli* BACE | CHO BACE |
| 38.41 | 31.03 | 83.32 |
| 26.50 | 45.80 | 85.20 |
| 32.84 | 31.86 | 78.07 |

The foregoing examples are illustrative of certain embodiments of the claimed invention, and do not serve to limit the invention in scope or spirit.

---

We claim:

1. An isolated polynucleotide comprising a sequence that encodes a polypeptide comprising human BACE-1 having the modification Pro33Lys.

2. An isolated polynucleotide comprising a polynucleotide sequence that encodes the amino acid sequence set forth in SEQ ID NO: 2.

3. An isolated polynucleotide comprising the nucleotide sequence of nucleotides 70–1365 of SEQ ID NO: 8.

4. An isolated polynucleotide consisting of the polynucleotide sequence of nucleotides 70–1365 of SEQ ID NO: 8.

5. A vector comprising the polynucleotide sequence of claim 1.

6. An expression vector comprising a polynucleotide sequence encoding a polypeptide comprising human BACE-1 having the modification Pro33Lys wherein said expression vector can produce the polypeptide when said expression vector is present in a compatible host cell, and when the host cell is cultured under conditions that allow for production of the polypeptide.

7. The expression vector of claim 6 wherein the polypeptide that is produced comprises the polypeptide sequence of SEQ ID NO: 2.

8. An isolated recombinant host cell comprising the expression vector of claim 6.

9. A method for producing a Pro33Lys-BACE1 polypeptide comprising the steps of: a) culturing the recombinant host cell of claim 8 under conditions that allow for the production of said polypeptide; and b) recovering the polypeptide from the culture.

10. The method of claim 9 wherein the host cell is *E. Coli*.

11. A method of producing a Pro33Lys-BACE-1 polypeptide comprising steps of: a) culturing the recombinant host cell of claim 8 under conditions that allow the production of Pro33Lys-BACE-1;) recovering the Pro33Lys-BACE-1 polypeptide from the cultured host cell; and c) diluting the polypeptide 20–50 fold with water having a temperature of about 1° C. to 15° C.

* * * * *

UNITED STATES PATENT AND TRADEMARK OFFICE
CERTIFICATE OF CORRECTION

PATENT NO. : 7,273,743 B2  Page 1 of 1
APPLICATION NO. : 10/372473
DATED : September 25, 2007
INVENTOR(S) : Kuo-Chen Chou and W. Jeffrey Howe It is certified that error appears in the above-identified patent and that said Letters Patent is hereby corrected as shown below:

Claim 11, column 44, line 29, insert --b-- after "Pro33Lys-BACE-1";

Signed and Sealed this

First Day of January, 2008

JON W. DUDAS
*Director of the United States Patent and Trademark Office*

SEQUENCE LISTING

<160> NUMBER OF SEQ ID NOS: 24

<210> SEQ ID NO 1
<211> LENGTH: 501
<212> TYPE: PRT
<213> ORGANISM: Homo sapiens
<220> FEATURE:
<221> NAME/KEY: MISC_FEATURE
<223> OTHER INFORMATION: Amino acid sequence of human BACE.

<400> SEQUENCE: 1

```
Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
            20                  25                  30

Gly Leu Gly Gly Ala Pro Leu Gly Leu Arg Leu Pro Arg Glu Thr Asp
        35                  40                  45

Glu Glu Pro Glu Glu Pro Gly Arg Arg Gly Ser Phe Val Glu Met Val
    50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
    130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
            180                 185                 190

Ser Leu Glu Pro Phe Phe Asp Ser Leu Val Lys Gln Thr His Val Pro
        195                 200                 205
```

```
Asn Leu Phe Ser Leu Gln Leu Cys Gly Ala Gly Phe Pro Leu Asn Gln
    210                 215                 220

Ser Glu Val Leu Ala Ser Val Gly Gly Ser Met Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
            260                 265                 270

Asp Leu Lys Met Asp Cys Lys Glu Tyr Asn Tyr Asp Lys Ser Ile Val
        275                 280                 285

Asp Ser Gly Thr Thr Asn Leu Arg Leu Pro Lys Lys Val Phe Glu Ala
    290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
            340                 345                 350

Thr Asn Gln Ser Phe Arg Ile Thr Ile Leu Pro Gln Gln Tyr Leu Arg
        355                 360                 365

Pro Val Glu Asp Val Ala Thr Ser Gln Asp Asp Cys Tyr Lys Phe Ala
    370                 375                 380

Ile Ser Gln Ser Ser Thr Gly Thr Val Met Gly Ala Val Ile Met Glu
385                 390                 395                 400

Gly Phe Tyr Val Val Phe Asp Arg Ala Arg Lys Arg Ile Gly Phe Ala
                405                 410                 415

Val Ser Ala Cys His Val His Asp Glu Phe Arg Thr Ala Ala Val Glu
            420                 425                 430

Gly Pro Phe Val Thr Leu Asp Met Glu Asp Cys Gly Tyr Asn Ile Pro
        435                 440                 445

Gln Thr Asp Glu Ser Thr Leu Met Thr Ile Ala Tyr Val Met Ala Ala
    450                 455                 460

Ile Cys Ala Leu Phe Met Leu Pro Leu Cys Leu Met Val Cys Gln Trp
465                 470                 475                 480

Arg Cys Leu Arg Cys Leu Arg Gln Gln His Asp Asp Phe Ala Asp Asp
                485                 490                 495

Ile Ser Leu Leu Lys
            500

<210> SEQ ID NO 2
<211> LENGTH: 432
<212> TYPE: PRT
<213> ORGANISM: Homo sapiens
<220> FEATURE:
<221> NAME/KEY: MISC_FEATURE
<223> OTHER INFORMATION: Amino acid sequence of human BACE with P33K
      mutation.

<400> SEQUENCE: 2

Thr Gln His Gly Ile Arg Leu Pro Leu Arg Ser Gly Leu Gly Gly Ala
1               5                   10                  15

Pro Leu Gly Leu Arg Leu Pro Arg Glu Thr Asp Glu Glu Pro Glu Glu
            20                  25                  30

Lys Gly Arg Arg Gly Ser Phe Val Glu Met Val Asp Asn Leu Arg Gly
        35                  40                  45
```

```
Lys Ser Gly Gln Gly Tyr Tyr Val Glu Met Thr Val Gly Ser Pro Pro
 50                  55                  60
Gln Thr Leu Asn Ile Leu Val Asp Thr Gly Ser Ser Asn Phe Ala Val
 65                  70                  75                  80
Gly Ala Ala Pro His Pro Phe Leu His Arg Tyr Tyr Gln Arg Gln Leu
                 85                  90                  95
Ser Ser Thr Tyr Arg Asp Leu Arg Lys Gly Val Tyr Val Pro Tyr Thr
            100                 105                 110
Gln Gly Lys Trp Glu Gly Glu Leu Gly Thr Asp Leu Val Ser Ile Pro
        115                 120                 125
His Gly Pro Asn Val Thr Val Arg Ala Asn Ile Ala Ala Ile Thr Glu
    130                 135                 140
Ser Asp Lys Phe Phe Ile Asn Gly Ser Asn Trp Glu Gly Ile Leu Gly
145                 150                 155                 160
Leu Ala Tyr Ala Glu Ile Ala Arg Pro Asp Asp Ser Leu Glu Pro Phe
                165                 170                 175
Phe Asp Ser Leu Val Lys Gln Thr His Val Pro Asn Leu Phe Ser Leu
            180                 185                 190
Gln Leu Cys Gly Ala Gly Phe Pro Leu Asn Gln Ser Glu Val Leu Ala
        195                 200                 205
Ser Val Gly Gly Ser Met Ile Ile Gly Gly Ile Asp His Ser Leu Tyr
    210                 215                 220
Thr Gly Ser Leu Trp Tyr Thr Pro Ile Arg Arg Glu Trp Tyr Tyr Glu
225                 230                 235                 240
Val Ile Ile Val Arg Val Glu Ile Asn Gly Gln Asp Leu Lys Met Asp
                245                 250                 255
Cys Lys Glu Tyr Asn Tyr Asp Lys Ser Ile Val Asp Ser Gly Thr Thr
            260                 265                 270
Asn Leu Arg Leu Pro Lys Lys Val Phe Glu Ala Ala Val Lys Ser Ile
        275                 280                 285
Lys Ala Ala Ser Ser Thr Glu Lys Phe Pro Asp Gly Phe Trp Leu Gly
    290                 295                 300
Glu Gln Leu Val Cys Trp Gln Ala Gly Thr Thr Pro Trp Asn Ile Phe
305                 310                 315                 320
Pro Val Ile Ser Leu Tyr Leu Met Gly Glu Val Thr Asn Gln Ser Phe
                325                 330                 335
Arg Ile Thr Ile Leu Pro Gln Gln Tyr Leu Arg Pro Val Glu Asp Val
            340                 345                 350
Ala Thr Ser Gln Asp Asp Cys Tyr Lys Phe Ala Ile Ser Gln Ser Ser
        355                 360                 365
Thr Gly Thr Val Met Gly Ala Val Ile Met Glu Gly Phe Tyr Val Val
    370                 375                 380
Phe Asp Arg Ala Arg Lys Arg Ile Gly Phe Ala Val Ser Ala Cys His
385                 390                 395                 400
Val His Asp Glu Phe Arg Thr Ala Ala Val Glu Gly Pro Phe Val Thr
                405                 410                 415
Leu Asp Met Glu Asp Cys Gly Tyr Asn Ile Pro Gln Thr Asp Glu Ser
            420                 425                 430

<210> SEQ ID NO 3
<211> LENGTH: 425
<212> TYPE: PRT
<213> ORGANISM: Homo sapiens
<220> FEATURE:
<221> NAME/KEY: MISC_FEATURE
```

<223> OTHER INFORMATION: Human beta-secretase zymogen.

<400> SEQUENCE: 3

```
Thr Gln His Gly Ile Arg Leu Pro Leu Arg Ser Gly Leu Gly Gly Ala
1               5                   10                  15

Pro Leu Gly Leu Arg Leu Pro Arg Glu Thr Asp Glu Glu Pro Glu Glu
            20                  25                  30

Pro Gly Arg Arg Gly Ser Phe Val Glu Met Val Asp Asn Leu Arg Gly
        35                  40                  45

Lys Ser Gly Gln Gly Tyr Tyr Val Glu Met Thr Val Gly Ser Pro Pro
    50                  55                  60

Gln Thr Leu Asn Ile Leu Val Asp Thr Gly Ser Ser Asn Phe Ala Val
65                  70                  75                  80

Gly Ala Ala Pro His Pro Phe Leu His Arg Tyr Tyr Gln Arg Gln Leu
                85                  90                  95

Ser Ser Thr Tyr Arg Asp Leu Arg Lys Gly Val Tyr Val Pro Tyr Thr
            100                 105                 110

Gln Gly Lys Trp Glu Gly Glu Leu Gly Thr Asp Leu Val Ser Ile Pro
        115                 120                 125

His Gly Pro Asn Val Thr Val Arg Ala Asn Ile Ala Ala Ile Thr Glu
130                 135                 140

Ser Asp Lys Phe Phe Ile Asn Gly Ser Asn Trp Glu Gly Ile Leu Gly
145                 150                 155                 160

Leu Ala Tyr Ala Glu Ile Ala Arg Pro Asp Asp Ser Leu Glu Pro Phe
                165                 170                 175

Phe Asp Ser Leu Val Lys Gln Thr His Val Pro Asn Leu Phe Ser Leu
            180                 185                 190

Gln Leu Cys Gly Ala Gly Phe Pro Leu Asn Gln Ser Glu Val Leu Ala
        195                 200                 205

Ser Val Gly Gly Ser Met Ile Ile Gly Ile Asp His Ser Leu Tyr
    210                 215                 220

Thr Gly Ser Leu Trp Tyr Thr Pro Ile Arg Arg Glu Trp Tyr Tyr Glu
225                 230                 235                 240

Val Ile Ile Val Arg Val Glu Ile Asn Gly Gln Asp Leu Lys Met Asp
                245                 250                 255

Cys Lys Glu Tyr Asn Tyr Asp Lys Ser Ile Val Asp Ser Gly Thr Thr
            260                 265                 270

Asn Leu Arg Leu Pro Lys Lys Val Phe Glu Ala Ala Val Lys Ser Ile
        275                 280                 285

Lys Ala Ala Ser Ser Thr Glu Lys Phe Pro Asp Gly Phe Trp Leu Gly
    290                 295                 300

Glu Gln Leu Val Cys Trp Gln Ala Gly Thr Thr Pro Trp Asn Ile Phe
305                 310                 315                 320

Pro Val Ile Ser Leu Tyr Leu Met Gly Glu Val Thr Asn Gln Ser Phe
                325                 330                 335

Arg Ile Thr Ile Leu Pro Gln Gln Tyr Leu Arg Pro Val Glu Asp Val
            340                 345                 350

Ala Thr Ser Gln Asp Asp Cys Tyr Lys Phe Ala Ile Ser Gln Ser Ser
        355                 360                 365

Thr Gly Thr Val Met Gly Ala Val Ile Met Glu Gly Phe Tyr Val Val
    370                 375                 380

Phe Asp Arg Ala Arg Lys Arg Ile Gly Phe Ala Val Ser Ala Cys His
385                 390                 395                 400
```

```
Val His Asp Glu Phe Arg Thr Ala Ala Val Glu Gly Pro Phe Val Thr
                405                 410                 415

Leu Asp Met Glu Asp Cys Gly Tyr Asn
            420                 425

<210> SEQ ID NO 4
<211> LENGTH: 391
<212> TYPE: PRT
<213> ORGANISM: Homo sapiens
<220> FEATURE:
<221> NAME/KEY: MISC_FEATURE
<223> OTHER INFORMATION: Human beta-secretase.

<400> SEQUENCE: 4

Arg Arg Gly Ser Phe Val Glu Met Val Asp Asn Leu Arg Gly Lys Ser
1               5                   10                  15

Gly Gln Gly Tyr Tyr Val Glu Met Thr Val Gly Ser Pro Pro Gln Thr
            20                  25                  30

Leu Asn Ile Leu Val Asp Thr Gly Ser Ser Asn Phe Ala Val Gly Ala
        35                  40                  45

Ala Pro His Pro Phe Leu His Arg Tyr Tyr Gln Arg Gln Leu Ser Ser
    50                  55                  60

Thr Tyr Arg Asp Leu Arg Lys Gly Val Tyr Val Pro Tyr Thr Gln Gly
65                  70                  75                  80

Lys Trp Glu Gly Glu Leu Gly Thr Asp Leu Val Ser Ile Pro His Gly
                85                  90                  95

Pro Asn Val Thr Val Arg Ala Asn Ile Ala Ala Ile Thr Glu Ser Asp
            100                 105                 110

Lys Phe Phe Ile Asn Gly Ser Asn Trp Glu Gly Ile Leu Gly Leu Ala
        115                 120                 125

Tyr Ala Glu Ile Ala Arg Pro Asp Asp Ser Leu Glu Pro Phe Phe Asp
    130                 135                 140

Ser Leu Val Lys Gln Thr His Val Pro Asn Leu Phe Ser Leu Gln Leu
145                 150                 155                 160

Cys Gly Ala Gly Phe Pro Leu Asn Gln Ser Glu Val Leu Ala Ser Val
                165                 170                 175

Gly Gly Ser Met Ile Ile Gly Gly Ile Asp His Ser Leu Tyr Thr Gly
            180                 185                 190

Ser Leu Trp Tyr Thr Pro Ile Arg Arg Glu Trp Tyr Tyr Glu Val Ile
        195                 200                 205

Ile Val Arg Val Glu Ile Asn Gly Gln Asp Leu Lys Met Asp Cys Lys
    210                 215                 220

Glu Tyr Asn Tyr Asp Lys Ser Ile Val Asp Ser Gly Thr Thr Asn Leu
225                 230                 235                 240

Arg Leu Pro Lys Lys Val Phe Glu Ala Ala Val Lys Ser Ile Lys Ala
                245                 250                 255

Ala Ser Ser Thr Glu Lys Phe Pro Asp Gly Phe Trp Leu Gly Glu Gln
            260                 265                 270

Leu Val Cys Trp Gln Ala Gly Thr Thr Pro Trp Asn Ile Phe Pro Val
        275                 280                 285

Ile Ser Leu Tyr Leu Met Gly Glu Val Thr Asn Gln Ser Phe Arg Ile
    290                 295                 300

Thr Ile Leu Pro Gln Gln Tyr Leu Arg Pro Val Glu Asp Val Ala Thr
305                 310                 315                 320

Ser Gln Asp Asp Cys Tyr Lys Phe Ala Ile Ser Gln Ser Ser Thr Gly
                325                 330                 335
```

```
Thr Val Met Gly Ala Val Ile Met Glu Gly Phe Tyr Val Val Phe Asp
            340                 345                 350

Arg Ala Arg Lys Arg Ile Gly Phe Ala Val Ser Ala Cys His Val His
            355                 360                 365

Asp Glu Phe Arg Thr Ala Ala Val Glu Gly Pro Phe Val Thr Leu Asp
            370                 375                 380

Met Glu Asp Cys Gly Tyr Asn
385                 390

<210> SEQ ID NO 5
<211> LENGTH: 372
<212> TYPE: PRT
<213> ORGANISM: Homo sapiens
<220> FEATURE:
<221> NAME/KEY: MISC_FEATURE
<223> OTHER INFORMATION: Human progastricsin.

<400> SEQUENCE: 5

Ala Val Val Lys Val Pro Leu Lys Lys Phe Lys Ser Ile Arg Glu Thr
1               5                   10                  15

Met Lys Glu Lys Gly Leu Leu Gly Glu Phe Leu Arg Thr His Lys Tyr
            20                  25                  30

Asp Pro Ala Trp Lys Tyr Arg Phe Gly Asp Leu Ser Val Thr Tyr Glu
            35                  40                  45

Pro Met Ala Tyr Met Asp Ala Ala Tyr Phe Gly Glu Ile Ser Ile Gly
        50                  55                  60

Thr Pro Pro Gln Asn Phe Leu Val Leu Phe Asp Thr Gly Ser Ser Asn
65                  70                  75                  80

Leu Trp Val Pro Ser Val Tyr Cys Gln Ser Gln Ala Cys Thr Ser His
                85                  90                  95

Ser Arg Phe Asn Pro Ser Glu Ser Ser Thr Tyr Ser Thr Asn Gly Gln
            100                 105                 110

Thr Phe Ser Leu Gln Tyr Gly Ser Gly Ser Leu Thr Gly Phe Phe Gly
            115                 120                 125

Tyr Asp Thr Leu Thr Val Gln Ser Ile Gln Val Pro Asn Gln Glu Phe
        130                 135                 140

Gly Leu Ser Glu Asn Glu Pro Gly Thr Asn Phe Val Tyr Ala Gln Phe
145                 150                 155                 160

Asp Gly Ile Met Gly Leu Ala Tyr Pro Ala Leu Ser Val Asp Glu Ala
                165                 170                 175

Thr Thr Ala Met Gln Gly Met Val Gln Glu Gly Ala Leu Thr Ser Pro
            180                 185                 190

Val Phe Ser Val Tyr Leu Ser Asn Gln Gln Gly Ser Ser Gly Gly Ala
            195                 200                 205

Val Val Phe Gly Gly Val Asp Ser Ser Leu Tyr Thr Gly Gln Ile Tyr
        210                 215                 220

Trp Ala Pro Val Thr Gln Glu Leu Tyr Trp Gln Ile Gly Ile Glu Glu
225                 230                 235                 240

Phe Leu Ile Gly Gly Gln Ala Ser Gly Trp Cys Ser Glu Gly Cys Gln
                245                 250                 255

Ala Ile Val Asp Thr Gly Thr Ser Leu Leu Thr Val Pro Gln Gln Tyr
            260                 265                 270

Met Ser Ala Leu Leu Gln Ala Thr Gly Ala Gln Glu Asp Glu Tyr Gly
            275                 280                 285

Gln Phe Leu Val Asn Cys Asn Ser Ile Gln Asn Leu Pro Ser Leu Thr
```

```
                      290                 295                 300
Phe Ile Ile Asn Gly Val Glu Phe Pro Leu Pro Ser Ser Tyr Ile
305                 310                 315                 320

Leu Ser Asn Asn Gly Tyr Cys Thr Val Gly Val Glu Pro Thr Tyr Leu
                325                 330                 335

Ser Ser Gln Asn Gly Gln Pro Leu Trp Ile Leu Gly Asp Val Phe Leu
                340                 345                 350

Arg Ser Tyr Tyr Ser Val Tyr Asp Leu Gly Asn Asn Arg Val Gly Phe
                355                 360                 365

Ala Thr Ala Ala
        370

<210> SEQ ID NO 6
<211> LENGTH: 371
<212> TYPE: PRT
<213> ORGANISM: Homo sapiens
<220> FEATURE:
<221> NAME/KEY: MISC_FEATURE
<223> OTHER INFORMATION: Human pepsinogen.

<400> SEQUENCE: 6

Leu Val Lys Val Pro Leu Val Arg Lys Lys Ser Leu Arg Gln Asn Leu
1               5                   10                  15

Ile Lys Asp Gly Lys Leu Lys Asp Phe Leu Lys Thr His Lys His Asn
                20                  25                  30

Pro Ala Ser Lys Tyr Phe Pro Glu Ala Ala Ala Leu Ile Gly Asp Glu
            35                  40                  45

Pro Leu Glu Asn Tyr Leu Asp Thr Glu Tyr Phe Gly Thr Ile Gly Ile
    50                  55                  60

Gly Thr Pro Ala Gln Asp Phe Thr Val Ile Phe Asp Thr Gly Ser Ser
65                  70                  75                  80

Asn Leu Trp Val Pro Ser Val Tyr Cys Ser Ser Leu Ala Cys Ser Asp
                85                  90                  95

His Asn Gln Phe Asn Pro Asp Asp Ser Ser Thr Phe Glu Ala Thr Ser
            100                 105                 110

Gln Glu Leu Ser Ile Thr Tyr Gly Thr Gly Ser Met Thr Gly Ile Leu
        115                 120                 125

Gly Tyr Asp Thr Val Gln Val Gly Gly Ile Ser Asp Thr Asn Gln Ile
    130                 135                 140

Phe Gly Leu Ser Glu Thr Glu Pro Gly Ser Phe Leu Tyr Tyr Ala Pro
145                 150                 155                 160

Phe Asp Gly Ile Leu Gly Leu Ala Tyr Pro Ser Ile Ser Ala Ser Gly
                165                 170                 175

Ala Thr Pro Val Phe Asp Asn Leu Trp Asp Gln Gly Leu Val Ser Gln
            180                 185                 190

Asp Leu Phe Ser Val Tyr Leu Ser Ser Asn Asp Asp Ser Gly Ser Val
        195                 200                 205

Val Leu Leu Gly Gly Ile Asp Ser Ser Tyr Tyr Thr Gly Ser Leu Asn
    210                 215                 220

Trp Val Pro Val Ser Val Glu Gly Tyr Trp Gln Ile Thr Leu Asp Ser
225                 230                 235                 240

Ile Thr Met Asp Gly Glu Thr Ile Ala Cys Ser Gly Gly Cys Gln Ala
                245                 250                 255

Ile Val Asp Thr Gly Thr Ser Leu Leu Thr Gly Pro Thr Ser Ala Ile
            260                 265                 270
```

```
Ala Ile Asn Ile Gln Ser Asp Ile Gly Ala Ser Glu Asn Ser Asp Gly
        275                 280                 285

Glu Met Val Ile Ser Cys Ser Ser Ile Asp Ser Leu Pro Asp Ile Val
        290                 295                 300

Phe Thr Ile Asp Gly Val Gln Tyr Pro Leu Ser Pro Ser Ala Tyr Ile
305                     310                 315                 320

Leu Gln Asp Asp Ser Cys Thr Ser Gly Phe Glu Gly Met Asp Val
                325                 330                 335

Pro Thr Ser Ser Gly Glu Leu Trp Ile Leu Gly Asp Val Phe Ile Arg
            340                 345                 350

Gln Tyr Tyr Thr Val Phe Asp Arg Ala Asn Asn Lys Val Gly Leu Ala
            355                 360                 365

Pro Val Ala
        370

<210> SEQ ID NO 7
<211> LENGTH: 455
<212> TYPE: PRT
<213> ORGANISM: Homo sapiens
<220> FEATURE:
<221> NAME/KEY: MISC_FEATURE
<223> OTHER INFORMATION: Amino acid sequence of recombinant human BACE
      with P33K mutation expressed in E. coli.

<400> SEQUENCE: 7

Met Ala Ser Met Thr Gly Gly Gln Gln Met Gly Arg Gly Ser Met Ala
1               5                   10                  15

Gly Val Leu Pro Ala His Gly Thr Gln His Gly Ile Arg Leu Pro Leu
            20                  25                  30

Arg Ser Gly Leu Gly Gly Ala Pro Leu Gly Leu Arg Leu Pro Arg Glu
        35                  40                  45

Thr Asp Glu Glu Pro Glu Glu Lys Gly Arg Arg Gly Ser Phe Val Glu
    50                  55                  60

Met Val Asp Asn Leu Arg Gly Lys Ser Gly Gln Gly Tyr Tyr Val Glu
65                  70                  75                  80

Met Thr Val Gly Ser Pro Pro Gln Thr Leu Asn Ile Leu Val Asp Thr
                85                  90                  95

Gly Ser Ser Asn Phe Ala Val Gly Ala Ala Pro His Pro Phe Leu His
            100                 105                 110

Arg Tyr Tyr Gln Arg Gln Leu Ser Ser Thr Tyr Arg Asp Leu Arg Lys
        115                 120                 125

Gly Val Tyr Val Pro Tyr Thr Gln Gly Lys Trp Glu Gly Glu Leu Gly
    130                 135                 140

Thr Asp Leu Val Ser Ile Pro His Gly Pro Asn Val Thr Val Arg Ala
145                 150                 155                 160

Asn Ile Ala Ala Ile Thr Glu Ser Asp Lys Phe Phe Ile Asn Gly Ser
                165                 170                 175

Asn Trp Glu Gly Ile Leu Gly Leu Ala Tyr Ala Glu Ile Ala Arg Pro
            180                 185                 190

Asp Asp Ser Leu Glu Pro Phe Phe Asp Ser Leu Val Lys Gln Thr His
        195                 200                 205

Val Pro Asn Leu Phe Ser Leu Gln Leu Cys Gly Ala Gly Phe Pro Leu
    210                 215                 220

Asn Gln Ser Glu Val Leu Ala Ser Val Gly Gly Ser Met Ile Ile Gly
225                 230                 235                 240

Gly Ile Asp His Ser Leu Tyr Thr Gly Ser Leu Trp Tyr Thr Pro Ile
```

```
                    245                 250                 255
Arg Arg Glu Trp Tyr Tyr Glu Val Ile Ile Val Arg Val Glu Ile Asn
            260                 265                 270

Gly Gln Asp Leu Lys Met Asp Cys Lys Glu Tyr Asn Tyr Asp Lys Ser
        275                 280                 285

Ile Val Asp Ser Gly Thr Thr Asn Leu Arg Leu Pro Lys Lys Val Phe
    290                 295                 300

Glu Ala Ala Val Lys Ser Ile Lys Ala Ala Ser Ser Thr Glu Lys Phe
305                 310                 315                 320

Pro Asp Gly Phe Trp Leu Gly Glu Gln Leu Val Cys Trp Gln Ala Gly
                325                 330                 335

Thr Thr Pro Trp Asn Ile Phe Pro Val Ile Ser Leu Tyr Leu Met Gly
            340                 345                 350

Glu Val Thr Asn Gln Ser Phe Arg Ile Thr Ile Leu Pro Gln Gln Tyr
        355                 360                 365

Leu Arg Pro Val Glu Asp Val Ala Thr Ser Gln Asp Asp Cys Tyr Lys
    370                 375                 380

Phe Ala Ile Ser Gln Ser Ser Thr Gly Thr Val Met Gly Ala Val Ile
385                 390                 395                 400

Met Glu Gly Phe Tyr Val Val Phe Asp Arg Ala Arg Lys Arg Ile Gly
                405                 410                 415

Phe Ala Val Ser Ala Cys His Val His Asp Glu Phe Arg Thr Ala Ala
            420                 425                 430

Val Glu Gly Pro Phe Val Thr Leu Asp Met Glu Asp Cys Gly Tyr Asn
        435                 440                 445

Ile Pro Gln Thr Asp Glu Ser
    450                 455

<210> SEQ ID NO 8
<211> LENGTH: 1365
<212> TYPE: DNA
<213> ORGANISM: Homo sapiens
<220> FEATURE:
<221> NAME/KEY: misc_feature
<223> OTHER INFORMATION: DNA sequence of recombinant human BACE with
      P33K mutation from E. coli.

<400> SEQUENCE: 8
atggctagca tgactggtgg acagcaaatg ggtcgcggat ccatggcggg agtgctgcct      60
gcccacggta cccaacatgg tattcgtctg ccactgcgta gcggtctggg tggtgctcca    120
ctgggtctgc gtctgccccg ggagaccgac gaagagcccg aggagaaagg ccggaggggc    180
agctttgtgg agatggtgga caacctgagg ggcaagtcgg ggcagggcta ctacgtggag    240
atgaccgtgg gcagcccccc gcagacgctc aacatcctgg tggatacagg cagcagtaac    300
tttgcagtgg gtgctgcccc ccaccccttc ctgcatcgct actaccagag gcagctgtcc    360
agcacatacc gggacctccg gaagggcgtg tatgtgccct acacccaggg caagtgggaa    420
ggggagctgg gcaccgacct ggtaagcatc cccatggcc caacgtcac tgtgcgtgcc     480 aacattgctg ccatcactga atcagacaag ttcttcatca acggctccaa ctgggaaggc    540
atcctggggc tggcctatgc tgagattgcc aggcctgacg actccctgga gcctttcttt    600
gactctctgg taaagcagac ccacgttccc aacctcttct ccctgcagct tgtggtgctg    660
ggcttccccc tcaaccagtc tgaagtgctg gcctctgtcg agggagcat gatcattgga    720 ggtatcgacc actcgctgta cacaggcagt ctctggtata cacccatccg gcgggagtgg    780
```

```
tattatgagg tcatcattgt gcgggtggag atcaatggac aggatctgaa aatggactgc    840
aaggagtaca actatgacaa gagcattgtg gacagtggca ccaccaacct tcgtttgccc    900
aagaaagtgt ttgaagctgc agtcaaatcc atcaaggcag cctcctccac ggagaagttc    960
cctgatggtt tctggctagg agagcagctg gtgtgctggc aagcaggcac caccccttgg   1020
aacattttcc cagtcatctc actctaccta atgggtgagg ttaccaacca gtccttccgc   1080
atcaccatcc ttccgcagca atacctgcgg ccagtggaaa atgtggccac gtcccaagac   1140
gactgttaca agtttgccat ctcacagtca tccacgggca ctgttatggg agctgttatc   1200
atggagggct tctacgttgt cttttgatcgg gcccgaaaac gaattggctt tgctgtcagc   1260
gcttgccatg tgcacgatga gttcaggacg gcagcggtgg aaggccctt tgtcaccttg    1320 gacatggaag actgtggcta caacattcca cagacagatg agtca                   1365
```

<210> SEQ ID NO 9
<211> LENGTH: 12
<212> TYPE: PRT
<213> ORGANISM: Homo sapiens
<220> FEATURE:
<221> NAME/KEY: MISC_FEATURE
<223> OTHER INFORMATION: T7-Tag.

<400> SEQUENCE: 9

Met Ala Ser Met Thr Gly Gly Gln Gln Met Gly Arg
1               5                   10

<210> SEQ ID NO 10
<211> LENGTH: 13
<212> TYPE: PRT
<213> ORGANISM: Homo sapiens
<220> FEATURE:
<221> NAME/KEY: MISC_FEATURE
<223> OTHER INFORMATION: Synthetic peptide substrate with a P33K-BACE
     cleavage site.

<400> SEQUENCE: 10

Ser Glu Ile Ser Tyr Glu Val Glu Phe Arg Trp Lys Lys
1               5                   10

<210> SEQ ID NO 11
<211> LENGTH: 23
<212> TYPE: PRT
<213> ORGANISM: Homo sapiens
<220> FEATURE:
<221> NAME/KEY: MISC_FEATURE
<223> OTHER INFORMATION: Synthetic peptide substrate with a P33K-BACE
     cleavage site.

<400> SEQUENCE: 11

Gly Leu Thr Asn Ile Lys Thr Glu Glu Ile Ser Glu Ile Ser Tyr Glu
1               5                   10                  15

Val Glu Phe Arg Trp Lys Lys
            20

<210> SEQ ID NO 12
<211> LENGTH: 13
<212> TYPE: PRT
<213> ORGANISM: Homo sapiens
<220> FEATURE:
<221> NAME/KEY: MISC_FEATURE
<223> OTHER INFORMATION: Synthetic peptide substrate with a P33K-BACE
     cleavage site.

<400> SEQUENCE: 12

-continued

Ser Glu Val Asn Leu Asp Ala Glu Phe Arg Trp Lys Lys
1               5                   10

<210> SEQ ID NO 13
<211> LENGTH: 23
<212> TYPE: PRT
<213> ORGANISM: Homo sapiens
<220> FEATURE:
<221> NAME/KEY: MISC_FEATURE
<223> OTHER INFORMATION: Synthetic peptide substrate with a P33K-BACE
      cleavage site.

<400> SEQUENCE: 13

Gly Leu Thr Asn Ile Lys Thr Glu Glu Ile Ser Glu Val Asn Leu Asp
1               5                   10                  15

Ala Glu Phe Arg Trp Lys Lys
            20

<210> SEQ ID NO 14
<211> LENGTH: 33
<212> TYPE: DNA
<213> ORGANISM: Homo sapiens
<220> FEATURE:
<221> NAME/KEY: misc_feature
<223> OTHER INFORMATION: PCR forward primer for amplification of BACE.

<400> SEQUENCE: 14
ggcaggatcc atggcgggag tgctgcctgc cca                                33

<210> SEQ ID NO 15
<211> LENGTH: 34
<212> TYPE: DNA
<213> ORGANISM: Homo sapiens
<220> FEATURE:
<221> NAME/KEY: misc_feature
<223> OTHER INFORMATION: PCR reverse primer for amplification of BACE.

<400> SEQUENCE: 15
ggcaggatcc tatgactcat ctgtctgtgg aatg                               34

<210> SEQ ID NO 16
<211> LENGTH: 31
<212> TYPE: DNA
<213> ORGANISM: Homo sapiens
<220> FEATURE:
<221> NAME/KEY: misc_feature
<223> OTHER INFORMATION: PCR forward primer for amplification of BACE.

<400> SEQUENCE: 16
ggcaggatcc atggctggtg ttctgccagc t                                  31

<210> SEQ ID NO 17
<211> LENGTH: 20
<212> TYPE: DNA
<213> ORGANISM: Homo sapiens
<220> FEATURE:
<221> NAME/KEY: misc_feature
<223> OTHER INFORMATION: PCR reverse primer for amplification of BACE.

<400> SEQUENCE: 17
tgccactgtc cacaatgctc                                               20

<210> SEQ ID NO 18
<211> LENGTH: 33
<212> TYPE: DNA
<213> ORGANISM: Homo sapiens
<220> FEATURE:

<221> NAME/KEY: misc_feature
<223> OTHER INFORMATION: PCR reverse primer for amplification of BACE.

<400> SEQUENCE: 18
ggcaggatcc tatgactcat ctgtctgtgg aat                           33

<210> SEQ ID NO 19
<211> LENGTH: 20
<212> TYPE: DNA
<213> ORGANISM: Homo sapiens
<220> FEATURE:
<221> NAME/KEY: misc_feature
<223> OTHER INFORMATION: PCR forward primer for amplification of BACE.

<400> SEQUENCE: 19
gagcattgtg gacagtggca                                          20

<210> SEQ ID NO 20
<211> LENGTH: 21
<212> TYPE: DNA
<213> ORGANISM: Homo sapiens
<220> FEATURE:
<221> NAME/KEY: misc_feature
<223> OTHER INFORMATION: PCR forward primer for amplification of BACE.

<400> SEQUENCE: 20
ccgaggagaa aggccggagg g                                        21

<210> SEQ ID NO 21
<211> LENGTH: 21
<212> TYPE: DNA
<213> ORGANISM: Homo sapiens
<220> FEATURE:
<221> NAME/KEY: misc_feature
<223> OTHER INFORMATION: PCR reverse primer for amplification of BACE.

<400> SEQUENCE: 21
ccctccggcc tttctcctcg g                                        21

<210> SEQ ID NO 22
<211> LENGTH: 19
<212> TYPE: DNA
<213> ORGANISM: Homo sapiens
<220> FEATURE:
<221> NAME/KEY: misc_feature
<223> OTHER INFORMATION: PCR forward primer for amplification of BACE.

<400> SEQUENCE: 22
taatacgact cactatagg                                           19

<210> SEQ ID NO 23
<211> LENGTH: 19
<212> TYPE: DNA
<213> ORGANISM: Homo sapiens
<220> FEATURE:
<221> NAME/KEY: misc_feature
<223> OTHER INFORMATION: PCR reverse primer for amplification of BACE.

<400> SEQUENCE: 23
gctagttatt gctcagcgg                                           19

<210> SEQ ID NO 24
<211> LENGTH: 459
<212> TYPE: PRT
<213> ORGANISM: Homo sapiens
<220> FEATURE:
<221> NAME/KEY: MISC_FEATURE
<223> OTHER INFORMATION: Human recombinant BACE with 6-His tags.

<400> SEQUENCE: 24

```
Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
            20                  25                  30

Gly Leu Gly Gly Ala Pro Leu Gly Leu Arg Leu Pro Arg Glu Thr Asp
        35                  40                  45

Glu Glu Pro Glu Glu Pro Gly Arg Arg Gly Ser Phe Val Glu Met Val
50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
            180                 185                 190

Ser Leu Glu Pro Phe Phe Asp Ser Leu Val Lys Gln Thr His Val Pro
        195                 200                 205

Asn Leu Phe Ser Leu Gln Leu Cys Gly Ala Gly Phe Pro Leu Asn Gln
210                 215                 220

Ser Glu Val Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
            260                 265                 270

Asp Leu Lys Met Asp Cys Lys Glu Tyr Asn Tyr Asp Lys Ser Ile Val
        275                 280                 285

Asp Ser Gly Thr Thr Asn Leu Arg Leu Pro Lys Lys Val Phe Glu Ala
290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
            340                 345                 350

Thr Asn Gln Ser Phe Arg Ile Thr Ile Leu Pro Gln Gln Tyr Leu Arg
        355                 360                 365

Pro Val Glu Asp Val Ala Thr Ser Gln Asp Asp Cys Tyr Lys Phe Ala
370                 375                 380

Ile Ser Gln Ser Ser Thr Gly Thr Val Met Gly Ala Val Ile Met Glu
385                 390                 395                 400
```

-continued

```
Gly Phe Tyr Val Val Phe Asp Arg Ala Arg Lys Arg Ile Gly Phe Ala
            405                 410                 415

Val Ser Ala Cys His Val His Asp Glu Phe Arg Thr Ala Ala Val Glu
            420                 425                 430

Gly Pro Phe Val Thr Leu Asp Met Glu Asp Cys Gly Tyr Asn Ile Pro
        435                 440                 445

Gln Thr Asp Glu Ser His His His His His His
    450                 455
```